US011668676B2

(12) United States Patent
Yanik et al.

(10) Patent No.: US 11,668,676 B2
(45) Date of Patent: Jun. 6, 2023

(54) MICROFLUIDIC ACOUSTIC DEVICES AND METHODS

(71) Applicant: The Regents of the University of California, Oakland, CA (US)

(72) Inventors: Ahmet Ali Yanik, Santa Cruz, CA (US); Xiangchao Zhu, Santa Cruz, CA (US); Evan Peterson, Sebastopol, CA (US); Yixiang Li, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 312 days.

(21) Appl. No.: 16/886,438

(22) Filed: May 28, 2020

(65) Prior Publication Data
US 2020/0378925 A1 Dec. 3, 2020

Related U.S. Application Data

(60) Provisional application No. 62/861,839, filed on Jun. 14, 2019, provisional application No. 62/854,894, filed on May 30, 2019.

(51) Int. Cl.
B01L 3/00 (2006.01)
G01N 29/02 (2006.01)
(Continued)

(52) U.S. Cl.
CPC ...... G01N 29/022 (2013.01); B01L 3/502707 (2013.01); G01N 29/046 (2013.01); G01N 29/2437 (2013.01)

(58) Field of Classification Search
CPC ............... G01N 29/022; G01N 29/046; G01N 29/2437; B01L 3/502707; B01L 3/502;
(Continued)

(56) References Cited

U.S. PATENT DOCUMENTS 8,573,060 B2   11/2013  Huang et al.
10,040,011 B2 * 8/2018  Lipkens ................. B01D 43/00
(Continued)

FOREIGN PATENT DOCUMENTS

CN    105647799 A * 6/2016  ............ C12M 23/16
CN    107167603 A * 9/2017  ............ G01N 33/574
(Continued)

OTHER PUBLICATIONS

Guo, "Three-dimensional manipulation of single cells using surface acoustic waves", 2016, PNAS, vol. 113, No. 6, 7 pages (Year: 2016).*
(Continued)

Primary Examiner — Melanie Brown
Assistant Examiner — Jennifer H. Tieu
(74) Attorney, Agent, or Firm — Shweta Chandra; Bozicevic, Field & Francis LLP

(57) ABSTRACT

The present disclosure provides methods, microfluidic devices, and systems for isolating target particles from a sample containing or suspected of containing the target particles. The methods, microfluidic devices, and systems disclosed herein facilitate affinity-based isolation of target particles in a microfluidic channel by translating the target particles to the side walls of the microfluidic channel where capture agents that bind to the target particles are immobilized.

20 Claims, 18 Drawing Sheets

(51) Int. Cl.
  *G01N 29/04* (2006.01)
  *G01N 29/24* (2006.01)
(58) Field of Classification Search
  CPC .... B01L 3/502761; B01L 3/50; B01L 3/5027; B01L 3/502776; B01L 2400/0436
  See application file for complete search history.

(56) References Cited

U.S. PATENT DOCUMENTS

2017/0184583 A1* 6/2017 Beaumont ......... B01L 3/502707
2017/0232439 A1* 8/2017 Suresh .............. B01L 3/502761
                                                              435/30

FOREIGN PATENT DOCUMENTS

EP        2670856 B1 *  6/2018  .......... B01F 13/0059
WO  WO-2019034795 A1 *  2/2019  .......... B01F 13/0059

OTHER PUBLICATIONS

Shields, "Elastomeric Negative Acoustic Contrast Particles for Capture, Acoustophoretic Transport, and Confinement of Cells in Microfluidic Systems", 2014, Langmuir, vol. 30, 5 pages (Year: 2014).*
Translation of Description of CN107167603A, Zhang, 2017, Espacenet, 4 pages (Year: 2017).*
Translation of Description of CN105647799A, Wang, 2016, Espacenet, 4 pages (Year: 2016).*
Bruus (2011) "Acoustofluidics 1: Governing equations in microfluidics" Lab on a Chip, 11(22):3742-3751.
Ding et al. (2012) "Standing surface acoustic wave (SSAW) based multichannel cell sorting" Lab on a Chip, 12 (21)4228-4231.
Ding et al. (2013) "Surface acoustic wave microfluidics" Lab on a Chip, 13(18):3626-3649.
Lee et al. (2015) "Acoustic Purification of Extracellular Microvesicles" ACS nano, 9(3):2321-2327.
Li et al. (2015) "Acoustic separation of circulating tumor cells" PNAS, 112(16): 4970-4975.
Shi et al. (2008) "Focusing microparticles in a microfluidic channel with standing surface acoustic waves (SSAW)†" Lab on a Chip, 8(2):221-223.
Shi et al. (2009) "Continuous particle separation in a microfluidic channel via standing surface acoustic waves (SSAW)" Lab on a Chip, 9(23):3354-3359.
Shi et al. (2011) "Three-dimensional continuous particle focusing in a microfluidic channel via standing surface acoustic waves (SSAW)" Lab on a Chip, 11(14):2319-2324.
Stroock et al. (2002) "Chaotic Mixer for Microchannels" Science, 295(5555):647-651.
Wood et al. (2008) "Alignment of particles in microfluidic systems using standing surface acoustic waves" Applied Physics Letters, 92(4):044104.
Yeo and Friend (2014) "Surface Acoustic Wave Microfluidics" Annual Review of Fluid Mechanics, 46:379-406.

* cited by examiner

MICROFLUIDIC ACOUSTIC DEVICES AND METHODS

FEDERALLY SPONSORED RESEARCH

This invention was made with government support under grant nos. 1642502 and 1847733 awarded by the National Science Foundation. The government has certain rights in the invention.

INTRODUCTION

Microfluidic devices provide control and manipulation of fluids in microfluidic channels having micrometer sized dimensions. The devices useful for processing, detecting or analyzing particles of interest in a fluid sample. Applications of microfluidics include, e.g., immunoaffinity assays where an analyte flows through a microfluidic channel and binds to a capture agent specific for the analyte. In some instances, immunoaffinity assays can detect and isolate analytes such as rare cells in a sample. Rare cells are low-abundance cells in a larger population of cells. Rare cells in the blood stream include stem cells, fetal cells, endothelial progenitor cells, dendritic cells, antigen specific T cells or circulating tumor cells. Rare cells are difficult to detect against a large population of background cells (red blood and white blood cells.

As such, there is a need for improved microfluidic devices that fulfill these and other needs.

SUMMARY

The present disclosure provides methods, microfluidic devices, and systems for isolating target particles from a sample containing or suspected of containing the target particles. The methods, microfluidic devices, and systems disclosed herein facilitate affinity-based isolation of target particles in a microfluidic channel by translating the target particles to the bottom of the microfluidic channel where capture agents that selectively bind to the target particles are immobilized on the piezoelectric substrate.

Disclosed are methods of isolating a target particle from a fluid sample. Such methods involve introduction a sample that includes a target particle into a microfluidic channel of a microfluidic device. The microfluidic channel has an inner surface that includes a capture surface. The capture surface has a capture agent that specifically binds the target molecule immobilized to it. A vertical acoustic force is applied to the sample. The vertical acoustic force is generated by standing surface acoustic waves (SSAWs) and is configured to drive the target particle to the capture surface, thereby promoting the binding of the target particle to the capture agent immobilized on the capture surface. The methods also involve eluting the target particle from the capture agent.

Further disclosed is a module used in isolating a target particle from a fluid sample. The module includes a microfluidic channel that has an acoustic cavity. The acoustic cavity has at least one of its surfaces formed from an elastic material. The microfluidic channel also has a capture surface that is configured to accept a capture agent. The microfluidic channel also has two interdigitated transducers (IDT's) positioned across the width of the microfluidic channel. The IDT's are configured to generate traveling surface acoustic waves (SAWs) within the microfluidic channel. The SAWs, when interacting with a fluid sample present in the microfluidic channel in turn generate compressional bulk acoustic waves (BAWs) that are reflected at least two times in the acoustic cavity. The BAWs interfere with the SAWs and generate a vertical acoustic force in the microfluidic channel. The vertical acoustic force then drives the target particle towards the capture surface.

Also disclosed is a system used to isolate a target particle from a sample. The system involves a first module that is configured to remove particles smaller than the target particle from the sample. The first module includes a first microfluidic channel that has two IDT's positioned across the first microfluidic channel such that they can generate standing surface acoustic waves (SSAWs) within the first microfluidic channel. The second module of the system has a second microfluidic channel, a capture surface that is configured to accept a capture agent, and two IDT's positioned across the second microfluidic channel and configured to generate SSAWs within the second microfluidic channel. The second microfluidic channel has an acoustic cavity comprising an elastic material. The SSAWs generate a vertical acoustic force in the acoustic cavity that drives the target particle towards the capture surface.

DETAILED DESCRIPTION

Figure 1:
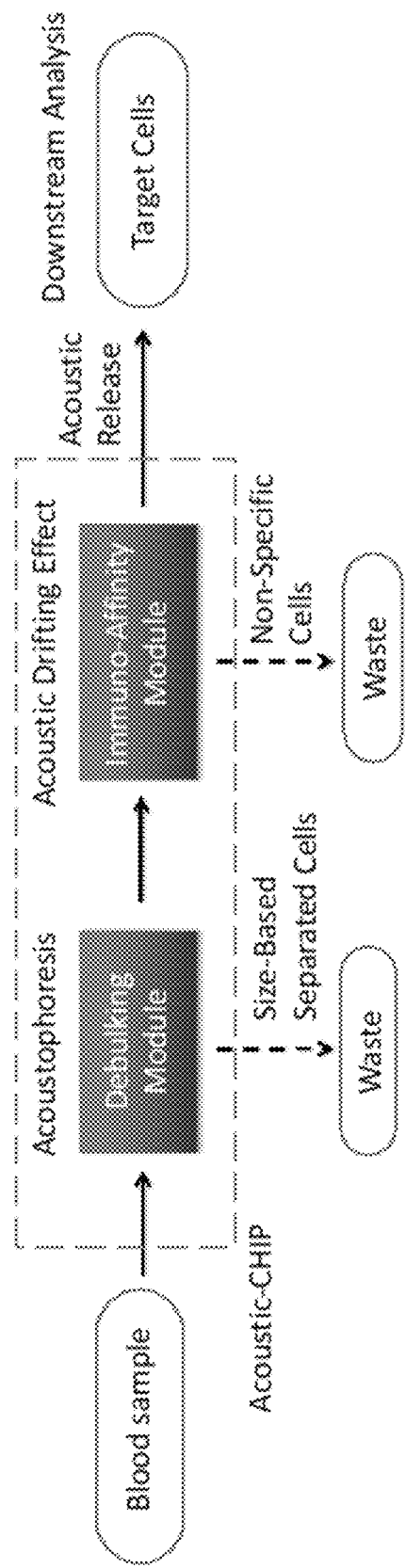
FIG. 1 depicts a schematic representation of an embodiment of the modules of the present disclosure.

The present disclosure provides methods of isolating a particle of interest from a sample. Also disclosed herein are microfluidic device and systems for implementing the methods disclosed herein.

Before exemplary embodiments of the present invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a particle of interest" includes a plurality of such particles and reference to "the sample" includes reference to one or more samples, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. To the extent such publications may set out definitions of a term that conflicts with the explicit or implicit definition of the present disclosure, the definition of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Method of Isolating Target Particle

The present disclosure provides methods of isolating a target particle from a sample. The method may include introducing a sample having or suspected of having a target particle into a microfluidic channel of a microfluidic device. The microfluidic channel may include an inner surface on which a capture agent that specifically binds to the target particle is immobilized. The method may further include a step of applying a vertical acoustic force, generated from a vertical quasi-standing acoustic wave, to the sample in the microfluidic channel, where the vertical acoustic force drives the target particle to the inner surface thereby promoting binding of the target particle to the capture agent at the capture surface. The method may further include a step of eluting the target particle bound to the capture agent. Various steps and aspects of the methods will now be described in greater detail below.

As used herein, the terms "sample", "test sample", "biological sample" refer to a fluid sample containing or suspected of containing a particle of interest. The sample may be derived from any suitable source. In some cases, the sample may include a liquid, fluent particulate solid, or fluid suspension of solid particles. In some cases, the sample may be processed prior to the method described herein. For example, the sample may be separated or purified from its source prior to analysis; however, in certain embodiments, an unprocessed sample containing the particle of interest may be assayed directly. The source of the particle of interest may be synthetic (e.g., produced in a laboratory), the environment (e.g., air, soil, etc.), an animal, e.g., a mammal, a plant, or any combination thereof. In a particular example, the source of a particle of interest is a human bodily substance (e.g., blood, serum, plasma, urine, saliva, sweat, sputum, semen, mucus, lacrimal fluid, lymph fluid, amniotic fluid, lung lavage, cerebrospinal fluid, feces, tissue, organ, or the like). The source of a particle of interest may include tissues such as, skeletal muscle tissue, liver tissue, lung tissue, kidney tissue, myocardial tissue, brain tissue, etc. The sample may be a liquid sample or a liquid preparation of a solid sample. In certain cases, the source of the sample may be an organ or tissue, such as a biopsy sample, which may be solubilized by tissue disintegration/cell lysis. A sample may be processed prior to performing immunoassay on the sample. In some instances, the sample may be concentrated, diluted, purified, amplified, etc. In particular embodiments, samples which may be assayed to determine the presence of a particle of interest in the sample may include biological fluid samples such as, for example, blood, plasma, or serum.

In some embodiments, the sample that is introduced into the microfluidic channel comprising the capture agents may be a sample enriched for the target particle by removing particles smaller than the target particle. In certain embodiments, the sample may be a whole blood sample that includes WBCs, RBCs, platelets, and target particles, such as, CTCs, stem cells, dendritic cell, endothelial progenitor cells, fibrocytes, T cells, fetal cells and the like. An enriched sample in which the ratio of the target particles to non-target particles (in this example, WBCs, RBCs, platelets) has been increased by decreasing the number of non-target particles may be produced by any technique known in the art. For example, a sample enriched for target particles present in a whole blood sample may be produced by lysing the RBCs. In another example, non-target particles smaller than the target particles may be removed by a prior acoustophoresis on the whole blood sample. Such an acoustophoresis technique may involve use of SSAWs as described in U.S. Pat. No. 8,573,060 (e.g., see FIG. 1), which is herein incorporated by reference in its entirety. Thus, in some embodiments, the enriched sample that is introduced into the microfluidic channel comprising immobilized capture agent may be a whole blood sample from which non-target particles, such as, RBCs and platelets have been removed by electrophoresis. This technique is further described in the section pertaining to microfluidic devices disclosed herein.

As used herein, the terms "particle of interest" or "target particle" are used interchangeably and refer to the particle being separated from a sample having or suspected of having the particle. A particle of interest may be a cell, a micelle, a vesicle, a droplet of different density from a fluid in which it is present, a bead (e.g., a microbead/microparticle or a nanobead/nanoparticle), etc. In some instances, particles may be labeled, for example, with a fluorescent marker, or otherwise functionalized. In some instances, a target particle is a cell of interest, e.g., circulating tumor cells, stem cells, endothelial progenitor cell, bacterial cells, etc. A "target particle" or a "particle of interest" encompasses a plurality of such particles. The subject methods and devices can also be used in a multiplex format where the sample includes two or more types of target particles and the capture surface(s) includes two or more types of capture agents. For example, the sample may include two different target particles, CTCs and stem cells, and the capture agents may include a first capture agent that specifically binds to CTCs and a second capture agent that specifically binds to the stem cells.

In some instances, the target particles have a diameter in the nanometer or micrometer range. In certain embodiments, the particles of interest have a diameter of 20 nm to 500 $\mu$m, such as 100 nm to 100 $\mu$m, 200 nm to 100 $\mu$m, 100 nm to 100 $\mu$m, 500 nm to 100 $\mu$m, 1 $\mu$m to 90 $\mu$m, 5 to 50 $\mu$m, 15 to 30 µm, 15 to 20 µm, or 100 nm-30 µm. In some instances, the particles of interest have a smaller diameter than 1 µm. In certain embodiments, the particles of interest are larger than red blood cells. The above-listed values and ranges for diameter refer to the values and ranges of the diameter of the target particle in physiological environment (e.g., pH 7.4, isotonic solution and the like). It is understood that the target particle may not be perfectly spherical and can be a spheroid, an ellipsoid, a prolate, or oblate. In certain embodiments, the diameter of the target particle refers to the longest straight line passing from side to side through the center of target particle.

In certain embodiments, the particles of interest have a low diffusion coefficient. By "diffusion coefficient" is meant a parameter indicative of the diffusion mobility of a substance and refers to the quantity of a substance that in diffusion from one region to another passes through each unit of cross section per unit of time when the volume-concentration gradient is unity. The diffusion coefficient of the particles of interest isolated in the subject methods and devices may be $1 \times 10^{-11}$ cm$^2$/s to $1 \times 10^{-5}$ cm$^2$/s, such as $6.5 \times 10^{-10}$ cm$^2$/s to $2.3 \times 10^{-8}$ cm$^2$/s. In certain embodiments, the particles of interest have a low diffusion coefficient that is lower than that of WBC, RBCs, platelets, etc.

In some instances, the compressibility of the particles of interest renders the particles susceptible to the acoustic force, as described in detail below. The term "compressibility" as used herein refers to compression of the target particle upon exposure to acoustic force. In some instances, the particles of interest have a compressibility of $2 \times 10^{-10}$ Pa$^{-1}$ to $5 \times 10^{-10}$ Pa$^{-1}$, such as $3.3 \times 10^{-10}$ Pa$^{-1}$ to $4.2 \times 10^{-10}$ Pa$^{-1}$.

The term "acoustophoresis" as used herein refers to the separation of particles by lateral acoustic forces generated by standing BAWs which include pressure nodes along the lateral direction in microfluidic channels at which larger particles are collected and separated from the smaller ones.

In certain aspects, the method microfluidic channel may be located between two IDTs, e.g., interdigitated electrodes. For example, two IDTs may be positioned across the width of the microfluidic channel and may be parallel to the longitudinal axis along the length of the microfluidic channel. In certain cases, there may be a plurality of microfluidic channels positioned between a pair of IDTs.

Aspects of the method may also include applying a vertical acoustic radiation force generated by BAWs to drive the particle of interest to the inner surface of a microfluidic channel. In some instances, the IDTs are positioned across from each other and are configured for generating surface acoustic waves that produce a vertical acoustic force in the microfluidic channel. The microfluidic channel may be acoustically coupled to the IDTs and may further include an elastic substrate that reflects acoustic waves. In certain embodiments, the IDTs may be disposed on a piezoelectric substrate and the microfluidic channel may be couple to the piezoelectric substrate. For example, the piezoelectric substrate may form a wall of the microfluidic channel. The microfluidic channel may also include an elastic substrate. For example, the microfluidic channel may be formed as an open channel in an elastic substrate and bonded onto the piezoelectric substrate thereby closing the open channel and creating a microfluidic channel that includes an inner surface formed from the piezoelectric substrate and remainder of the inner surface formed from the elastic substrate. The microfluidic channel may thus include an acoustic cavity for generating the vertical acoustic force applied to the sample. The vertical acoustic force may drive particles that are mostly in the center of the fluid flowing through the microfluidic channel towards the side walls of the channel. The terms "vertical acoustic force" and "vertical acoustic radiation force" are used herein interchangeably.

Figure 4A:
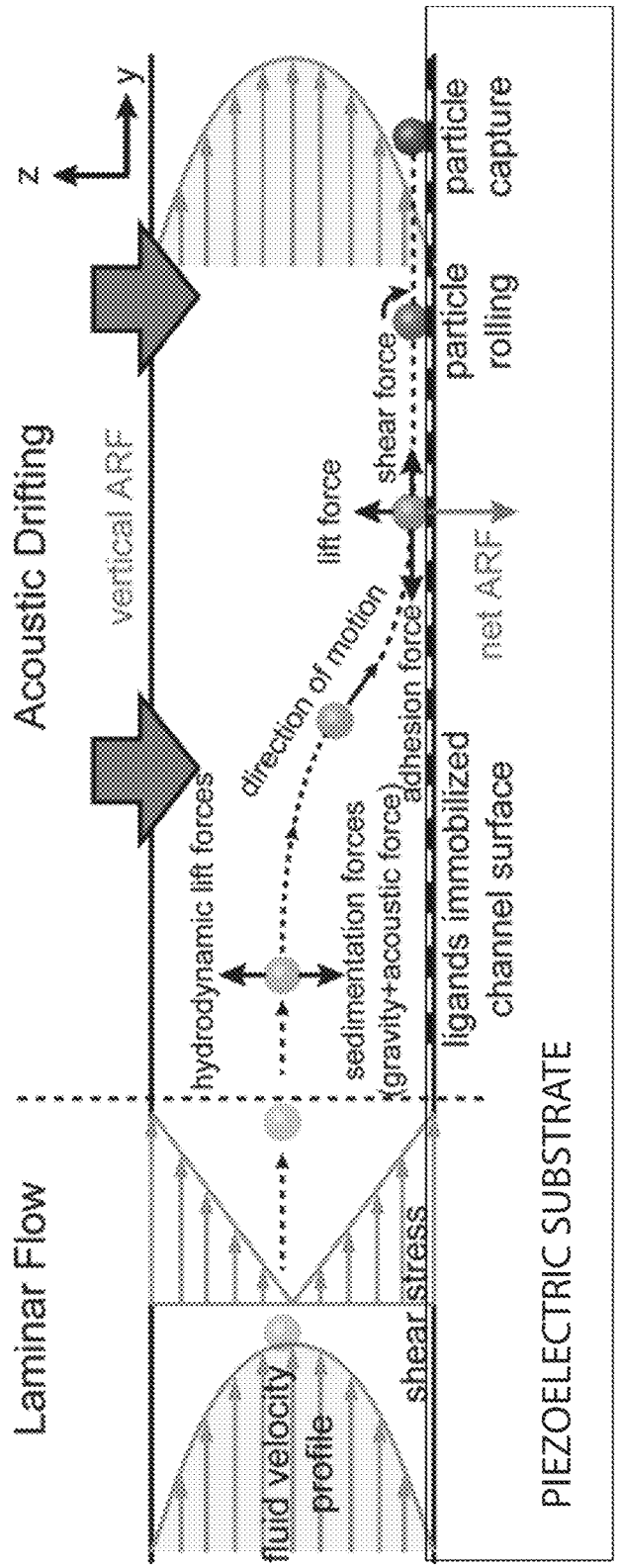
FIG. 4A depicts a schematic of the affinity-based isolation of cells using a vertical ARF, which is created along the height of the channel. A side view of the channel is shown here to help us to visualize vertical ARF along the height of the channel. In a conventional microfluidic channel, cells travel away from the channel walls closer to the center of the channel, where the fluidic flow is fastest (laminar flow profile). Vertical translation of cells in between different flow lines is only through random diffusion processes and generally very slow for larger particles (i.e., cells). In acoustic drifting effect (ADE) devices, ARF created along the height of the channel (vertical direction) pushes cells towards the substrate (e.g., a piezoelectric substrate) forming the bottom of the microfluidic channel and enables affinity-based capturing of specific cells using antibodies immobilized on the substrate.

FIG. 4A depicts a schematic of the affinity-based isolation of target particles using a vertical acoustic force.

Figure 5A:
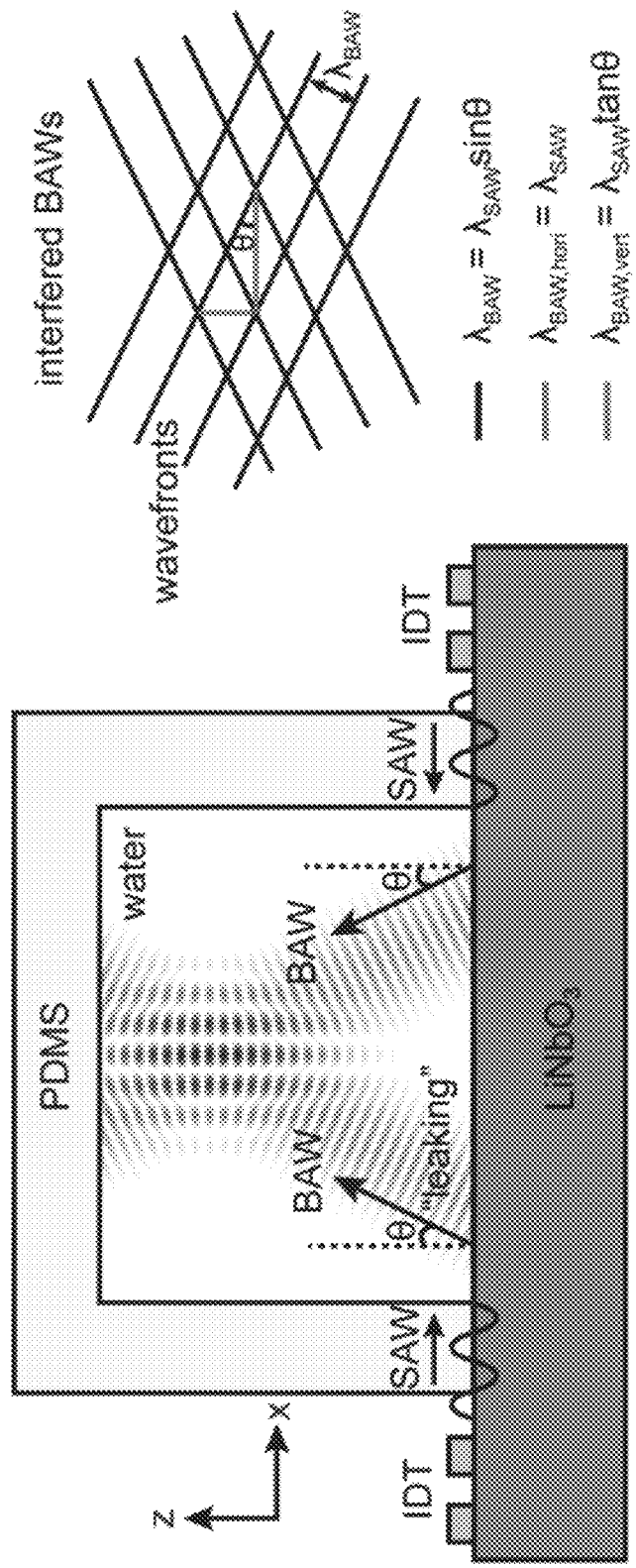
FIG. 5A depicts how horizontal and vertical ARFs emerge within an acoustic cavity created by integrating a piezoelectric substrate with a PDMS microfluidic channel IDTs on the either side of the channel creates two-counter propagating SAWs that leak into the solution at an angel θ to the surface normal and lead to BAWs propagating within the fluidic environment. Interference of the counter propagating BAWs in the lateral direction results in a standing BAW pattern along the width of the channel with a wavelength $\lambda_{BAW, hori} = \lambda_{SAW} \sin\theta / \sin\theta = \lambda_{SAW}$. In addition to this lateral standing wave, the vertical component of the BAW creates a quasi-standing wave along the height of the channel with a wavelength $\lambda_{BAW, vert} = \lambda_{SAW} \sin\theta / \cos\theta = \lambda_{SAW} \tan\theta$. This is due to the self-interference of BAW propagating in the vertical direction after getting reflected from impedance mismatched (PDMS and piezoelectric substrate) interfaces. Quasi-standing and standing BAW in the vertical and lateral directions lead to a complex acoustic pressure distribution that resembles to a baklava or diamond pattern.

FIG. 5A depicts an acoustic cavity created by coupling a piezoelectric substrate to a channel formed in a PDMS substrate. The leaked SAWs actuate the fluid inducing compressional acoustic bulk waves (BAWs). The superposition of these two BAWs propagating in opposite directions produces a pure standing BAW in the lateral direction along the channel width with a wavelength $\lambda_{BAW, hori} = \lambda_{SAW} \sin\theta / \sin\theta = \lambda_{SAW}$. In addition, IDTs create an upward propagating traveling BAW in the vertical direction with wavelength $\lambda_{BAW, vert} = \lambda_{SAW} \sin\theta / \cos\theta = \lambda_{SAW} \tan\theta$. Due to the acoustic impedance at different material interface along the vertical direction, the upward propagating traveling BAW experience a partial reflection (R) back to the fluidic environment. In this case, an acoustic cavity is formed in between the bottom piezoelectric substrate and PDMS ceiling. After multiple reflections between the perfectly reflective (piezoelectric substrate) and partially reflective (channel ceiling) "acoustic mirrors", a standing BAW in the vertical plane of the fluid is created. This vertical standing BAW with an amplitude associated with the acoustic reflection coefficient R is superimposed on the non-reflected traveling vertical BAW, constructing a quasi-standing acoustic wave in the vertical direction.

Figure 5B:
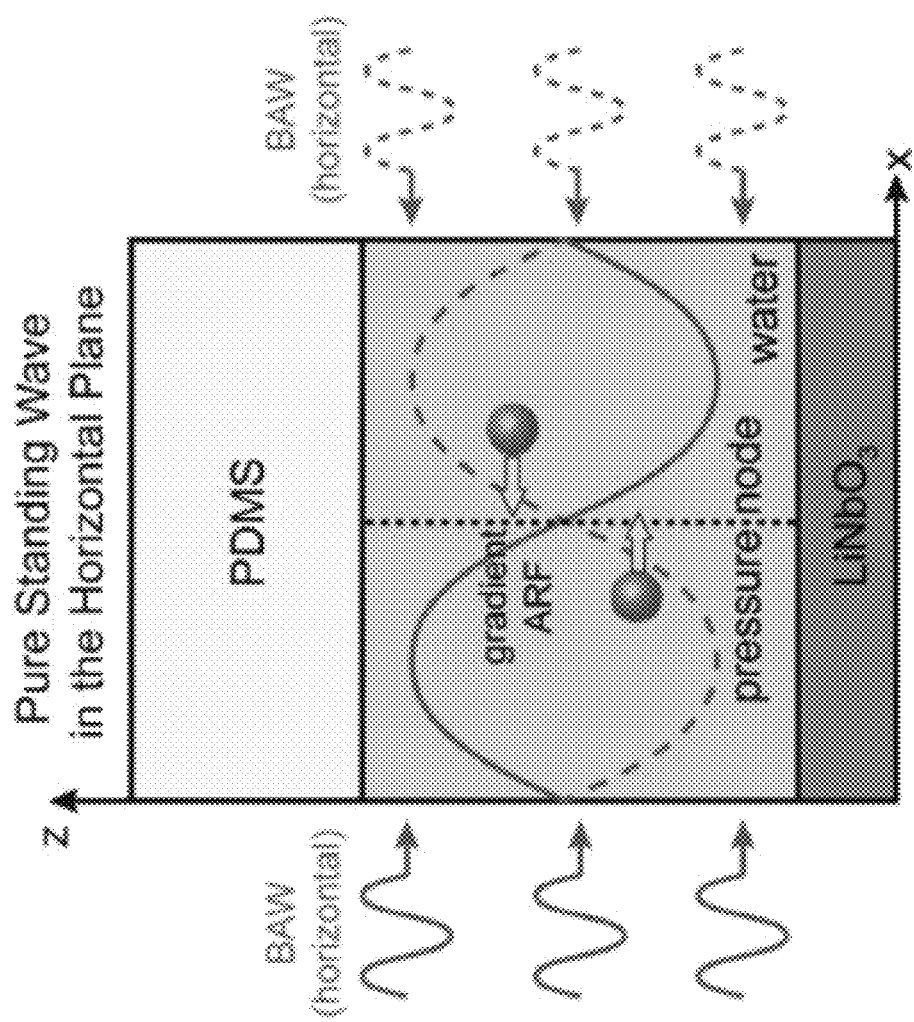
FIG. 5B illustrates the ARF created in the lateral direction as a result of lateral standing BAW. The lateral standing BAW pushes particles towards pressure nodes along the width of the channel (x-direction).

FIG. 5B illustrates lateral direction standing BAW pushing particles to the pressure node, which is commonly used in acoustophoresis (size-based separation) applications.

Figure 5C:
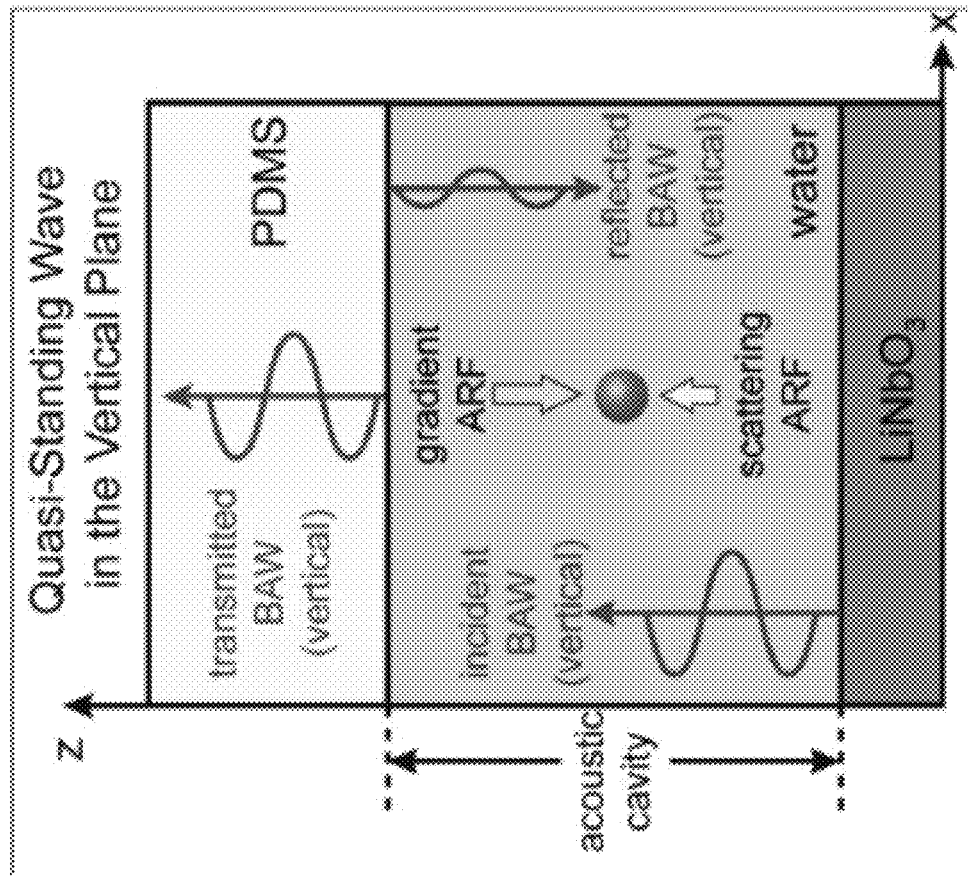
FIG. 5C illustrates the ARF created in the vertical direction as a result of vertical quasi-standing BAW, which is a superposition of a vertical traveling and vertical standing BAW components. Suspended particles in this quasi-standing wave field are subject to two different types of acoustic radiation forces (ARFs): scattering ARF resulted from the non-reflected vertical traveling BAW component, gradient ARF imposed by the vertical standing BAW component. By carefully choosing the reflection coefficient R based on the selections of the materials for the solution, piezoelectric substrate and channel, the dominant role of the force can be tuned from the scattering ARF to the gradient ARF, or vice versa. When the gradient ARF dominates the scattering ARF, particles are drifted towards the piezoelectric substrate, the acoustic drifting effect.

FIG. 5C illustrates emergence of acoustic drifting effect (ADE) in the vertical direction due to the quasi-standing acoustic wave along the height of the channel Particles in this quasi-standing wave field are subjected to two different types of acoustic radiation forces (ARFs): scattering ARF due to the vertical traveling BAW component, gradient ARF imposed by the vertical standing BAW component. For particle's sizes which are much smaller than wavelength, the gradient ARF in a pure standing acoustic wave (corresponding to |R|=100%) is about two orders of magnitude greater than the scattering ARF in a pure traveling acoustic wave (or |R|=0). When the fluid has a relatively high acoustic impedance with respect to the channel roof, a π phase change is resulted during the wave reflection process. This sudden phase jump giving rise to a gradient ARF that points towards downwards induces a vertical acoustic force driving the particles to the surface of the piezoelectric substrate, the acoustic drifting effect (ADE). By carefully choosing the reflection coefficient R based on the selections of the materials for the fluid and channel ceiling, the dominant role of the force can be tuned from the scattering ARF to the gradient ARF, or vice versa.

Figure 5D:
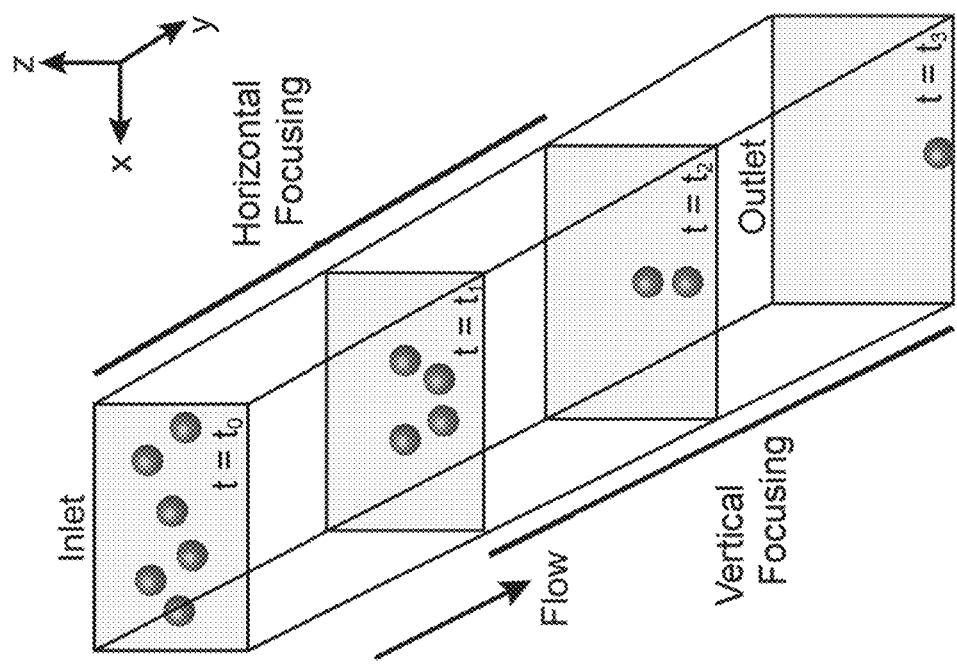
FIG. 5D shows a simulation showing the effect of the lateral and vertical ARFs acting on particles traveling along the channel. Particles initially entering at random locations in the inlet plane are focused both along channel width at a pressure node (X=0) due to lateral ARF and along the channel height at the bottom channel surface (Z=0) due to the vertical ARF. Illustration on the right aims to help visualizing the three-dimensional motion of the particles.
Figure 5D:
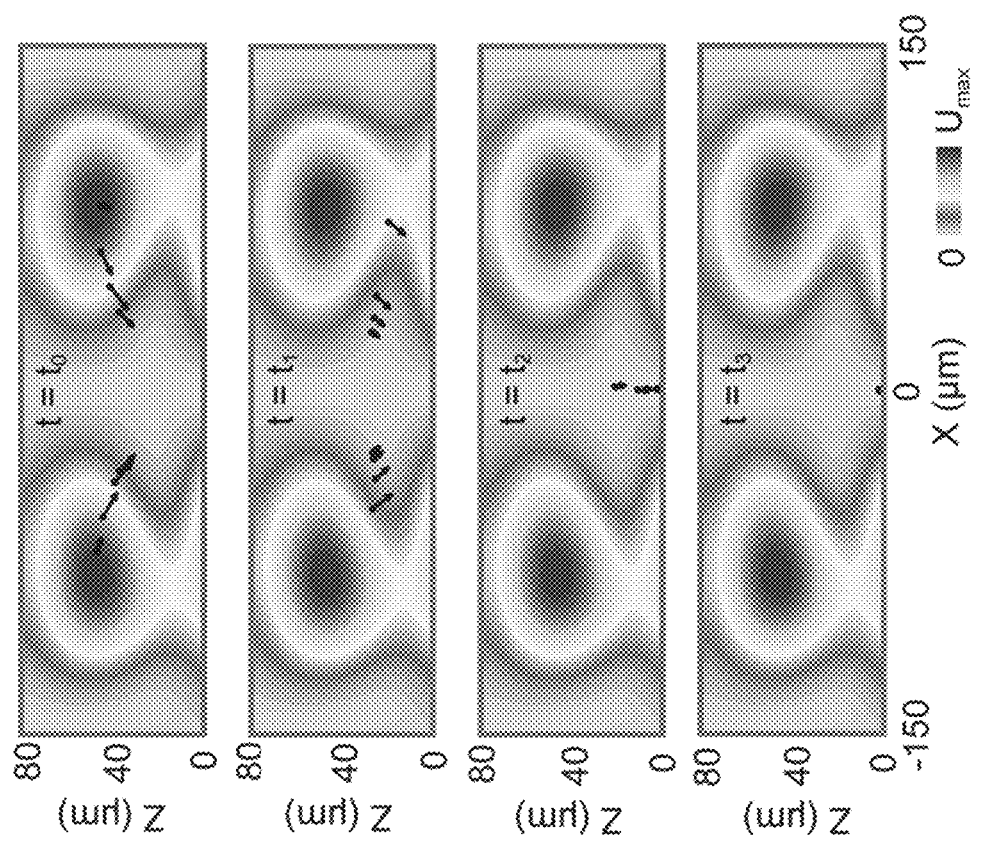

FIG. 5D shows the calculated Gor'kov potential field and particle trajectories bringing them to the lowest potential locations on the piezoelectric surface as particles travel along the channel.

The microfluidic channel includes capture agents that bind to the particles of interest immobilized on the inner surface of the channel and the vertical acoustic force pushes the particles towards the piezoelectric surface within the microfluidic channel.

Figure 8:
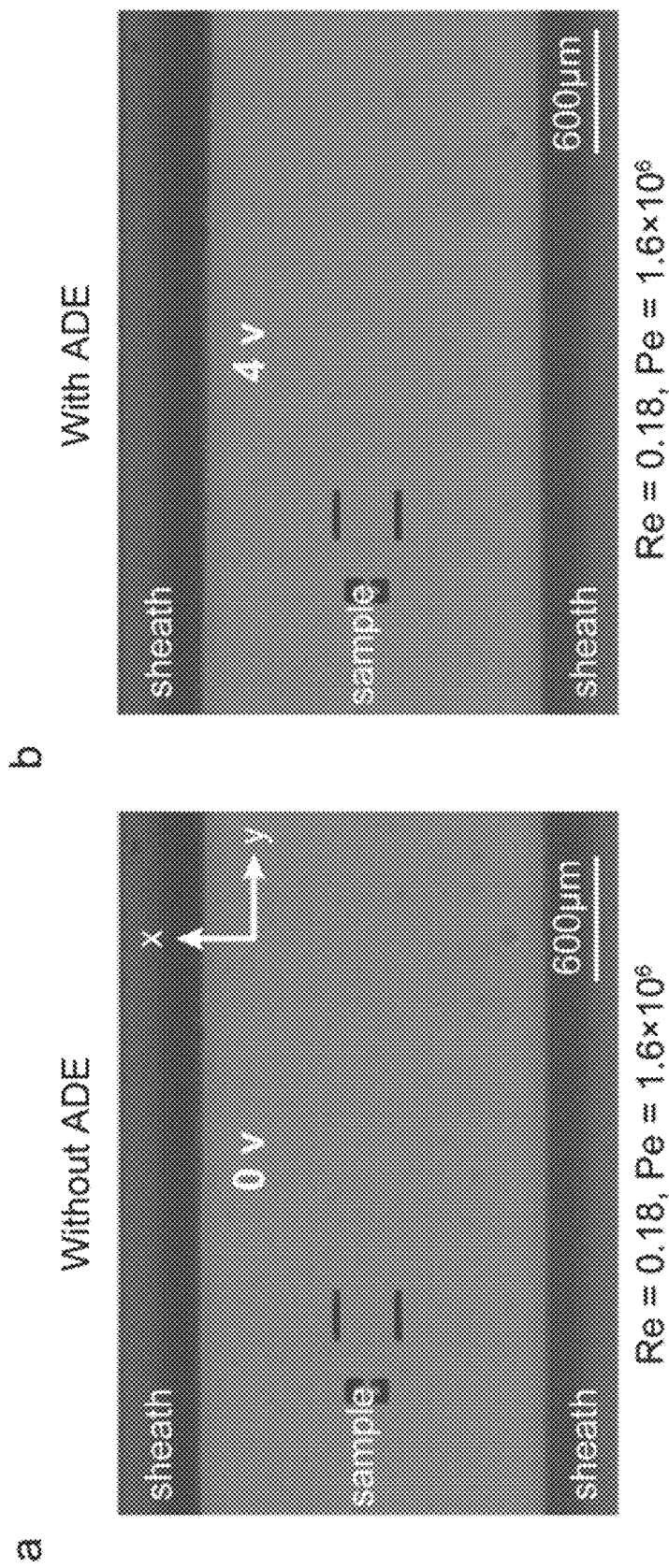
FIG. 8 illustrates that the laminar profile of a fluid flowing through a microchannel is not affected by the absence (a) or presence (b) of acoustic waves (SAWs). Acoustic jetting effects are too weak to mix laminar flow lines.

In certain instances, before the IDTs are activated to generate SAWs, the fluid flowing through the microfluidic channel is in a laminar flow and most of the particles in the fluid are located towards the center of the flowing fluid and hence are having a minimal interaction with the side walls of the microfluidic channel upon activation of the IDTs, the laminar flow profile is maintained (see FIG. 8). However, particles are subjected to a vertical ARF in the acoustic cavity which drives the particles towards the side walls and hence closer to the capture agents immobilized on the inner surface (see FIG. 4A and FIG. 4B).

In some instances, the particles of interest are pushed in the acoustic cavity away from the center and towards the side by the vertical acoustic force. In some instances, the IDTs generate SAWs in a substrate which provides a vertical acoustic force field within a microfluidic channel proximate to the substrate. In some instances, the force field may be perpendicular to the plane of a capture surface of the microfluidic channel. The vertical acoustic force may be the result of surface acoustic waves generated from a pair of IDTs positioned across the width of the microfluidic channel. The surface acoustic waves from the IDTs may propagate through a piezoelectric substrate that forms at least one inner surface of the microfluidic channel. When a propagating SAW reaches a boundary between the solid piezoelectric substrate and the liquid sample, SAW can efficiently "leak" their energies into the fluid. The leaky SAW radiates e into the fluid at the Rayleigh angle, given by the acoustic law of refraction and actuate the fluid inducing compressional acoustic bulk waves (BAWs). The BAWs will be reflected from the walls of the microfluidic channel formed from an elastic substrate, such as, PDMS.

In some instances, the particles of interest are bound to the capture agents immobilized on a region on the inner wall of the microfluidic channel. The region of the surface of the inner wall of the microfluidic channel at which the capture agent is immobilized is referred to as capture region or capture surface. The capture agent may be immobilized on the inner surface of microfluidic device according to any method known in the art. In some instances, the "capture agent" refers to one member of a pair of molecules that have binding specificity for one another. One member of the pair of molecules may have an area on its surface, or a cavity which specifically binds to an area on the surface of, or a cavity in, the other member of the pair of molecules. Thus, the members of the pair have the property of binding specifically to each other to produce a binding complex. In some embodiments, the affinity between specific binding members in a binding complex is characterized by a $K_d$ (dissociation constant) of $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less. In some embodiments, the specific binding members specifically bind with high avidity. By high avidity is meant that the binding member specifically binds with an apparent affinity characterized by an apparent $K_d$ of $10 \times 10^{-9}$ M or less, such as $1 \times 10^{-9}$ M or less, $3 \times 10^{-10}$ M or less, $1 \times 10^{-10}$ M or less, $3 \times 10^{-11}$ M or less, $1 \times 10^{-11}$ M or less, $3 \times 10^{-12}$ M or less or $1 \times 10^{-12}$ M or less. In some embodiments, the capture agent may be a polypeptide, e.g., an antibody or a fragment thereof or a receptor that specifically binds to the target particle.

In some instances, the method include detecting the captured particles at the capture surface. For example, the captured particles may be visualized by detectably labeling the captured particles. Detectable labels may include a fluorescent label. The detectable label may be attached to the captured particles by using a labeled molecule that binds to the captured particles, such as, a labeled antibody. In some instances, the method may optionally include introducing a buffer into the microfluidic channel prior to detecting the captured particles. In some aspects, the method may include eluting the particles of interest. In certain embodiments, the buffer removes any particles that are not bound to the capture surface. Any suitable buffer may be used as is known in the art.

In certain embodiments, the subject methods include eluting particles of interest bound to the capture surface. The particles of interest may be eluted by dissociating them from the capture surface along the inner surface of the microfluidic channel. In some instances, the eluting may be performed by applying heat to particles of interest bound to the capture surface, thereby releasing the particles of interest. In some instances, the heat is provided by sound waves through, e.g., a radiofrequency amplifier or by a Peltier device. In some instance, the capture surface includes a protein and/or polymer layer that melts at temperatures between 20° C. and 45° C. to facilitate the release of the particles of interest. In some instance, ARFs can be used to help breaking molecular bonds and lifting of the particles from the captured surfaces. In some instances, the second module is configured to collect released particles of interest into a solution. The solution comprising the released target particles may be analyzed within the microfluidic channel by any suitable technique (e.g. spectral analysis using a fluorescence detector, a cytometry, a spectrophotometer and the like) or may be collected and analyzed in a separate device using any suitable technique.

Microfluidic Device

The present disclosure also provides microfluidic devices which find use, e.g., in practicing the subject methods. In certain aspects, the microfluidic device may be an isolation module. In other aspects, the microfluidic device may have two modules: a first module for enriching the target particles by removing non-target particles present in the sample and a second module for isolating the target particle by capturing the target particle or for isolating the target particle by capturing the non-target particles. In some embodiments, the first module may be in fluid communication with second module.

Isolation Module

In certain aspects, the microfluidic device may be an isolation module. The isolation module may include a microfluidic channel comprising an acoustic cavity comprising at least two surfaces formed from an elastic material, the microfluidic channel comprising a capture surface comprising a capture agent that specifically binds the target particle; and two interdigitated transducers (IDTs) positioned across the microfluidic channel and configured to generate SAWs, wherein the SAWs refract upon interaction with a fluid sample present in the microfluidic channel thereby generating the compressional bulk acoustic waves (BAWs), wherein the vertical BAWs are reflected a plurality of times in the acoustic cavity, wherein the reflected waves interfere with the vertical acoustic waves and generate a vertical acoustic force in the microfluidic channel, wherein the vertical acoustic force drives the target particle from the center of the microfluidic channel towards the capture surface.

In certain embodiments, the capture surface may located at or downstream to the location at which the vertical acoustic force is generated. The capture agent(s) may be immobilized on one or more surfaces of the microfluidic channel. The microfluidic channel may have any suitable configuration and the cross section of the microfluidic channel may be circular or rectangular.

In certain embodiments, the sample may be an enriched sample from which some of the non-target particles have been removed. The sample may be introduced into the microfluidic channel through an inlet and the isolated target particles may exit the microfluidic channel through an outlet. Wash buffers and elution buffers, if used, may also introduced into the microfluidic channel vial the inlet.

Other aspects of the isolation module are further described in the context of microfluidic device comprising first and second modules. However, it is understood that the isolation module may be a stand-alone microfluidic device that is not integrated with another module that enriches the sample before the sample is introduced into the isolation module.

Integrated Modules

In some instances, the method includes prior to introducing the sample into the isolation module that includes a capture region, separating target particles from non-target particles in a sample based on size by acoustophoresis. In some instances, a first module that is configured for separating target particles from non-target particles in a sample based on size by acoustophoresis may be integrated with &-second module that includes a microchannel comprising a capture region. The level of integration of the first and second module may vary. In some instances, the first module may be fluidically connected to the second module. Fluidic connection may be established by channel (e.g., a tubing) that connects the microfluidic channels of the two modules. In some instances, the modules may be formed on a single piezoelectric substrate.

In some aspects, the first module is configured to remove particles smaller than the target particle from the sample and includes a first microfluidic channel comprising a proximal end and a distal end, and two interdigitated transducers (IDTs) located across the first microfluidic channel and configured to generate standing surface acoustic waves (SSAWs) within the first microfluidic channel; and a second module, the second module comprising a second microfluidic channel comprising a proximal end and a distal end, and a capture agent immobilized on a capture surface of the second microfluidic channel, and two interdigitated transducers (IDTs) located across the second microfluidic channel and configured to generate standing surface acoustic waves within the second microfluidic channel, wherein the second microfluidic channel comprises an acoustic cavity comprising an elastic material, wherein the surface acoustic waves generate a vertical acoustic force in the acoustic cavity, wherein the vertical acoustic force drives the target particle towards the capture surface.

In certain aspects, the microfluidic device for use in the subject method may include a first module, e.g., a standing surface acoustic wave (SSAW) chip. The first module may include surface acoustic force generators, e.g., interdigitated transducers (IDTs), for generating SSAWs within one or more microfluidic channels. Once an RF signal is applied to the IDTs, e.g., to a pair of IDTs positioned across the microchannel, two series of surface acoustic waves (SAW) propagate in opposite directions toward the fluid sample inside the microchannel. The two counterpropagating SAWs actuate the fluid inducing compressional acoustic bulk waves (BAWs). The constructive interference of the two counter-propagating BAWs in lateral direction results in the formation of a standing BAW along the channel width, as well as the periodic distribution of the pressure nodes and anti-nodes in the microchannel (regions of minimum and maximum pressure amplitude, respectively). These pressure fluctuations result in acoustic radiation forces that act laterally on the particles. As a result, the suspended particles inside the channel are forced toward either the pressure nodes or antinodes, depending on the size, density and compressibility of the particles and the medium.

Figure 3A:
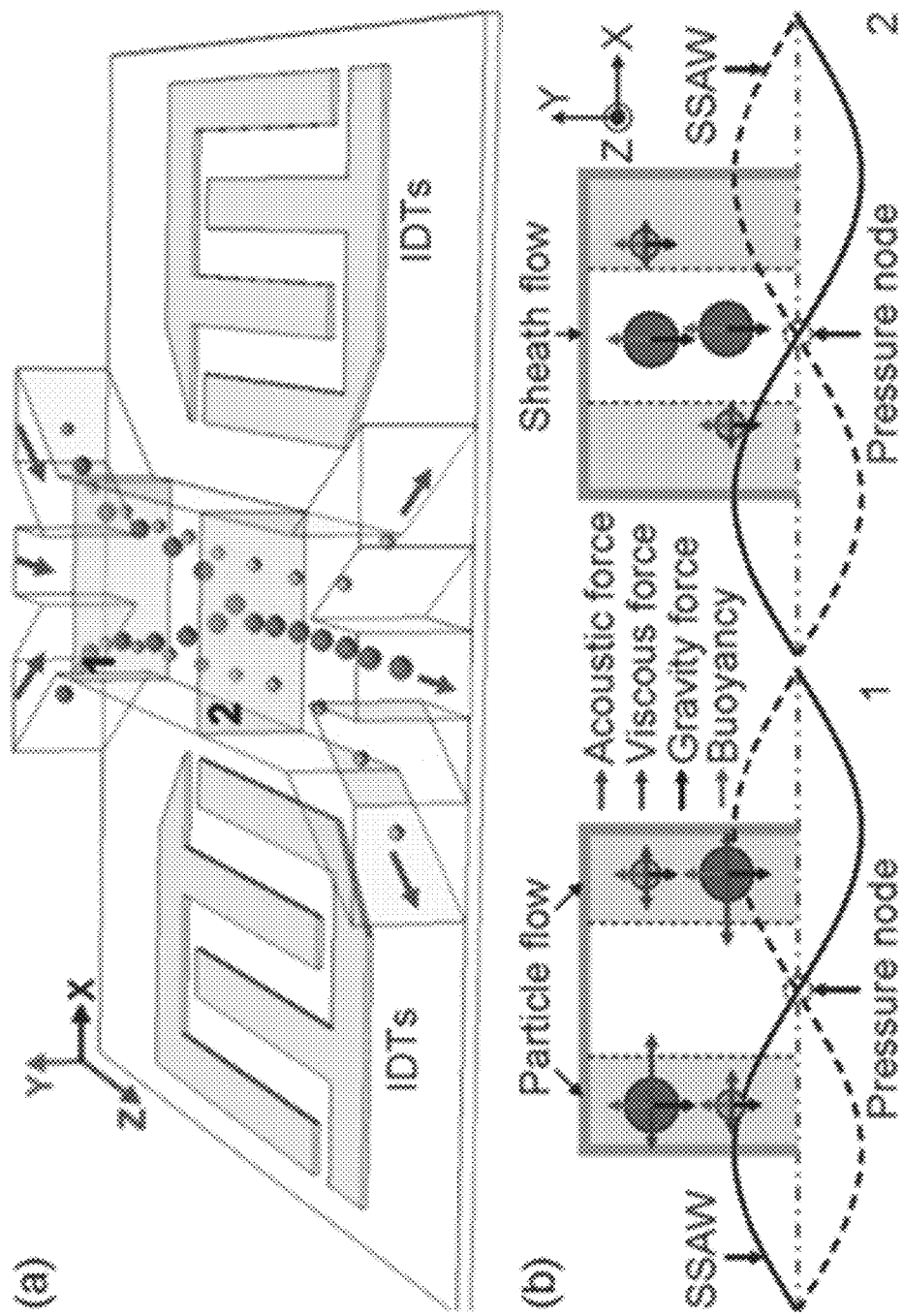
FIG. 3A illustrates a size-based separation module (acoustophoresis) as known in the art. Different size particles feel varying acoustic radiation forces (ARF) along the channel width (in a lateral direction). Initially, all particles enter the microfluidic region from the edges. As particles travel along the channel, larger size particles, experiencing a larger lateral ARF, get collected along the acoustic pressure nodes and separated from the small ones, which still travel close to the edges.

In certain embodiments, the IDTs of the first module may apply an acoustic force to sample to separate particles based on size. In some instances, the acoustic force is applied such that larger particles having a diameter of 1 µm or larger, e.g., 8 to 50 µm, flow through an area approximately at the center of the microfluidic channel while smaller particles, e.g., red blood cells, platelets, etc., flow through the channel at approximately the sides of the channel. In some instances, targeted particles are smaller than 1 µm diameter, e.g. 30 nm-500 nm. In some instances, the microfluidic channel is branched at the distal end such that the smaller particles flowing at approximately the sides of the microfluidic channel are directed away from the larger sized particles flowing at approximately the center of the microfluidic channel. In some instances, the smaller particles exit the microfluidic channel in a separate fluid stream than the larger particle. For example, the sample may be introduced into the first microfluidic channel of the first module (the first module is also referred to herein as debulking or enrichment module) using inlets that feed the sample towards the side of the first microfluidic channel, as illustrated in FIG. 1. The first module may include two IDTs placed on a substrate and positioned across the width of one or more microfluidic channels. The IDTs may generate SAWs, e.g., SSAWs, within one or more microfluidic channels, as illustrated in FIG. 3A. A sample containing particles of interest may be passed through the one or more microfluidic channels such that the particles in the sample experience a lateral force generated by the SAWs. In some instances, the larger particles experience the force to a greater extent and diffuse towards the one or more nodes of the lateral standing BAWs (FIG. 3B) located at the center of the microfluidic channel.

The outlet of the first microfluidic channel may also be branched and may include one or more side outlets through which the smaller particles travelling closer to the side walls of the first microfluidic channel may exit and a central outlet through which the larger molecules focused in the central region of the first microfluidic channel exit.

In some cases, the microfluidic channel of the first module is in fluid communication with the microfluidic channel of a second module of the device. The second module may include a microfluidic channel that receives fluid from the microfluidic channel of the first module. In some instances, the distal end of the microfluidic channel of the first module is joined with the proximal end of the microfluidic channel of the second module. In some instances, the central outlet of the first microfluidic channel may be connected to a proximal end of the second microfluidic channel present in the second module. The second module is also referred to as the isolation module or capture module which may be a stand-alone device or may be fluidically connected to the first module.

The second module may include a second microfluidic channel, a capture agent immobilized on a capture surface of the second microfluidic channel, and interdigitated electrodes configured to generate a standing bulk acoustic waves within the second microfluidic channel, where the standing bulk acoustic waves generate a vertical acoustic force, where the vertical acoustic force drives the particle of interest towards the capture surface.

In certain embodiments, the second module generates quasi-standing BAWs that produce a vertical acoustic force field. The second module may include one or more IDTs for generating SAWs that lead to BAWs. The IDTs may be fabricated on a substrate and positioned around one or more microfluidic channels having an inner surface. The IDTs may generate BAWs within one or more microfluidic channels. In some instances, the second module manipulates particles by the acoustic drift effect of the vertical acoustic force field. When a traveling SAW travels through a piezoelectric substrate, radiates into the fluidic environment of the microfluidic channel, and reaches the liquid medium, the liquid absorbs part of the SAW's energy and may refract it in the form of compressional acoustic bulk waves (BAWs). The BAWs may be reflected back upon reaching the elastic material of the channel, e.g., impedance mismatched boundaries of a PDMS channel. In some instances, the BAWs are generated in a manner such that a vertical acoustic force acts upon the particles of interest within the microfluidic channel. The particles within the microfluidic channel may be pushed towards the sides, walls, or inner surface of the channel by the vertical acoustic force.

The IDTs may be arranged on a substrate in any manner suitable to generate the SAWs of the subject methods. The device may include one microfluidic channel positioned between two or more interdigitated electrodes on a substrate. In some instances, the device includes a pair of IDTs that are positioned across from one another and parallel to the direction of flow of sample in the microchannel. In some instances, the IDTs are coplanar. In some instances, the IDTs have a facing configuration. In certain embodiments, the IDTs are placed on the substrate such that the direction of the SAWs is parallel to the direction of flow of the microfluidic channel. In certain embodiments, the IDTs are arranged in parallel or at a slanted angle to the microfluidic channel. The interdigitated electrodes may be positioned such that the electrodes generate SAWs that are parallel to the direction of flow through the microfluidic channel. In some instances, the microfluidic channel may be positioned within 1 mm to 1 cm of the acoustic field, such as within 0.1 mm to 1 mm of the acoustic field. In some instances, the direction of flow is not at an oblique angle to the direction of the SAWs, e.g., the standing BAWs generated by the counter propagating SAWs. The SAW direction may be a direction aligned with the generally linear anti-nodes and nodes of the BAWs. By "oblique" is meant an angle between 0 and 90 degrees and between 90 and 180 degrees, not including 0, 90, or 180.

The IDTs may have any dimensions suitable for generating the SAWs of the subject methods. In some instances, the IDT finger overlap or aperture width (W) is 10 µm to 5 mm. The operating frequency of the acoustic force field generated by the IDTs may be −13.33 MHz to 666.5 MHz. The wavelength of the acoustic field may be 50 µm to 2 mm or 2 µm to 400 µm, such as 100 µm to 300 µm. In some instances, the node to node distance of the standing surface acoustic wave generated by the IDTs is 2l2=100 µm to 10 mm, 50 µm to 1 mm or 50 µm to 150 µm.

In certain embodiments, the IDTs of the device, e.g., one or both of the first and second modules may be replaced with liquid metal containing microfluidic channels. In some instances, the liquid metal containing channels may be shaped similarly to or in the same form of IDTs. In some instances, the liquid metal is a liquid metal alloy. Liquid metals of interest include, but are not limited to, gallium, indium, mercury, lead, tin, bismuth, cadmium, lithium, calcium, magnesium, etc., and alloys thereof.

According to one embodiment, the dimensions of the microfluidic channel of the second module are suitable for generating a vertical acoustic force. In some instances, the channel may have a width of 1 µm to 5 cm, such as 100 µm to 1 mm. In some instances, the height, normal to the substrate, is 0.4 µm to 13 mm, such as 10 µm to 11 mm, e.g., 20 µm to 50 µm, 100 µm to 500 µm, 30 µm-500 µm, 30 µm-300 µm, 30 µm to 1 mm, or 40 µm-150 µm. The length of the channel may be 50 µm to 10 cm or 0.5 mm to 10 cm, such as 1 mm to 1 cm, 1 mm to 5 mm, or 2 mm to 8 mm. The volume of the channel may be 1 µL to 500 µL.

In some instances, the second module may use a vertical acoustic force to push particles of interest to the inner surface of the microfluidic channel, towards the walls of the microfluidic channel, or towards a capture surface within the microfluidic channel. The particles may be bound by capture agents immobilized on the inner surface of the channel. The particles of interest may be, e.g., the particles of interest isolated from the sample in the first module of the device. A capture surface may be located within the microfluidic channel of the second module. The capture surface may be present along the inner surface of the microfluidic channel. In some instances, capture agents may be immobilized on the capture surface of the microfluidic channel. In some instances, the capture surface is the inner surface of the channel on which capture agents are immobilized. In some instances, the capture surface is a coating formed on an inner surface of the microfluidic channel. The particles of interest may be bound by capture agents immobilized on the inner surface according to any method known in the art. Examples of capture agents suitable for use in the capture surface include, but are not limited to, receptors, antibodies, a nucleic acid, etc.

In some cases, the second module includes one or more capture agents. The capture agents may specifically bind to markers on the particles of interest. The capture agents may include, but are not limited to, antibodies, such as monoclonal antibodies and/or antibodies specific for markers of CTCs, e.g., EpCAM. In some instances, the capture agents are located within the microfluidic channel. In some instances, the capture agents are present on the inner surfaces of the microfluidic channel. The capture surface may include a capture agent immobilized on at least one surface of the channel by any method known in the art. In certain embodiments, the capture agents are present on one or more walls of the microfluidic channel. In some instances, the capture agents are present on the bottom or top inner surface of the microfluidic channel. In some instances, the capture agents are present on the inner surface of the side walls of the microfluidic channel. In certain embodiments, the capture agents are present in a coating on an inner surface of the microfluidic channel.

In certain embodiments, the capture agent binds specifically to the particle of interest. By "specifically bind" or "binding specificity," it is meant that the capture agent binds the particle of interest with specificity sufficient to differentiate between the particle of interest and other components or contaminants of the test sample. The capture agent, according to one embodiment, may be an antibody that binds specifically to an epitope of a particle of interest.

As used herein, the terms "antibody" and "antibody molecule" are used interchangeably and refer to a protein consisting of one or more polypeptides substantially encoded by all or part of the recognized immunoglobulin genes. The recognized immunoglobulin genes, for example in humans, include the kappa (κ), lambda (l), and heavy chain genetic loci, which together comprise the myriad variable region genes, and the constant region genes mu (u), delta (d), gamma (g), sigma (e), and alpha (a) which encode the IgM, IgD, IgG, IgE, and IgA isotypes respectively. An immunoglobulin light or heavy chain variable region consists of a "framework" region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, (1991)). The numbering of all antibody amino acid sequences discussed herein conforms to the Kabat system. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen. The term antibody is meant to include full-length antibodies and may refer to a natural antibody from any organism, an engineered antibody, or an antibody generated recombinantly for experimental, therapeutic, or other purposes as further defined below.

In some cases, the capture agent is an antibody-binding agent. Antibody-binding agents and antibody fragments of interest include, but are not limited to, Fab, Fab', F(ab')2, Fv, scFv, or other antigen-binding subsequences of antibodies, either produced by the modification of whole antibodies or those synthesized de novo using recombinant DNA technologies. Antibodies may be monoclonal or polyclonal and may have other specific activities on cells (e.g., antagonists, agonists, neutralizing, inhibitory, or stimulatory antibodies). It is understood that the antibodies may have additional conservative amino acid substitutions which have substantially no effect on antigen binding or other antibody functions. In certain embodiments, the specific binding member is a Fab fragment, a $F(ab')_2$ fragment, a scFv, a diabody or a triabody. In certain embodiments, the specific binding member is an antibody. In some cases, the specific binding member is a murine antibody or binding fragment thereof. In certain instances, the specific binding member is a recombinant antibody or binding fragment thereof.

In certain embodiments, the microfluidic device may be formed using two or more substrates. In some instances, a module of the device includes a substrate upon which IDTs are fabricated. In certain embodiments, the substrate may be a piezoelectric substrate. Piezoelectric substrates include, but are not limited to, lithium niobate, lithium tantalite, lead zirconium titanate, zinc oxide, aluminum nitride, polymers such as polyvinylidene fluoride (PVdF) or other fluoropolymer, crystalline quartz, or other material. In some instances, the substrate includes a strong piezoelectric material, such as 128° YX $LiNbO_3$ or 36° YX $LiTaO_3$. In some instances, the substrate may be a dielectric substrate. Dielectric substrates include, but are not limited to, ceramics, plastics, glass, mica, etc.

The module of the microfluidic device may include at least one microfluidic channel having a proximal end and a distal end, e.g., an inlet and outlet. In certain embodiments, the first module includes two or more channels, e.g., three, four, five, six, seven, eight, nine, or ten or more channels. In some instances, the channels are positioned on the module in parallel. The channel may be configured to receive a fluid sample including particles of interest.

In certain embodiments, the microfluidic channels have dimensions suitable for use in the subject methods. The channels of the device may be microchannels, e.g., having at least one cross-sectional dimension less than 1 millimeter, such as less than 500 microns, and in some instances, less than 100 microns. In some instances, the height, normal to the substrate, is 1 µm to 500 µm, such as 10 µm to 100 µm. In some instances, the channel may have a width of 1 µm to 500 µm, such as 100 µm to 300 µm. In certain embodiments, the channel width is designed to cover only one pressure node such that particles are focused at the node when the standing BAW is generated. In some cases, the channel width is designed to cover two or more pressure nodes along the width direction. In some instances, the channel may have a length of 0.5 to 1 cm, such as 1 to 5 mm. In certain embodiments, the channels may have a sub-femtoliter volume, femtoliter volume, sub-nanoliter volume, nanoliter volume, sub-microliter volume, or microliter volume. The channel dimensions are not limited to these dimensions, but may depend upon the extent of the SAW BApropagation area on a substrate and BAW standing wave condition requirements which depends on the acoustic wave frequency.

The channels of the microfluidic device may be formed in a polymer or other material (i.e. materials that be fabricated using injection molding). The channel may be formed by a molded polymer element on a substrate. In some instances, a trench or other structure may be formed in a polymer and the placed against a substrate to form a channel materials for the polymer include, but are not limited to polydimethylsiloxane (PDMS), silicone polymers, or other polymers having desired mechanical, chemical, and/or physical properties. In certain embodiments, a polymer may be selected so as to be effectively transparent to radiation used to analyze, count, or otherwise characterize the particles in the channel. In some instances, the channel may be formed in a soft polymer, i.e., a polymer in which features can be formed by soft lithography.

The microfluidic channel may have any cross-sectional shape. In some instances, the channel is substantially circular or rectangular (e.g., square) in cross-section. The microfluidic channel may be formed such that the inner surfaces of the microfluidic channel are substantially planar. The inner surface of the microfluidic channel may be substantially smooth to facilitate laminar flow of fluids through the microfluidic channel. In some embodiments, the microfluidic channel may have a substantially rectangular cross section and may include a bottom portion formed by the substrate on which the acoustic waves travel (e.g., the substrate on which the IDT electrodes are positioned) and two side walls and a top portion, where the two side walls and the top portion are formed from any suitable substrate, such as, a substrate that reflects acoustic waves. In some aspects, the walls of the microfluidic channel may be formed from the same material. In some aspects, the walls of the microfluidic channel may be formed from different materials, e.g., the bottom wall may be a first material and the other three walls may be made from a second material different from the first material. In some aspects, the second material may not propagate acoustic waves to a significant extent and may reflect the acoustic waves to a significant extent. In some embodiments, the microfluidic channel may have a substantially rectangular cross section and may include a first side wall that is formed from a piezoelectric substrate and three side walls formed from an elastic material. In some embodiments, the capture agent may be immobilized on the bottom wall or the top wall of the channel or both. In some embodiments, the capture agent may be immobilized on the piezoelectric substrate or the elastic substrate or both. In some instances, the capture agent may be immobilized in the microfluidic channel at a location at or downstream to the location(s) where the vertical acoustic force is applied to the sample.

In some instances, the microfluidic channel is branched at one or both ends such that the channel may have multiple inlets/outlets.

In certain aspects, the microfluidic device includes one or more interdigitated electrodes, i.e. interdigitated transducers (IDTs). In some instances, the IDTs may be present on the surface of a substrate of a module of the device. An IDT may include a finger like periodic pattern of parallel in-plane electrodes. An IDT may include two interlocking comb-shaped electrodes, the electrodes being provided by a metal or other conducting coatings supported by the substrate. The spatial periodicity, or spatial wavelength, of the IDT is the distance between the centerlines of adjacent finger pairs.

SAWs may be created when a single transducer or electrode is activated. The strength of an outputted SAW can be controlled by changing the overlap of the electrodes, number of finger pairs, their periodicity, the finger pattern, and the power input. The SAW transducer is most efficient when the excitation frequency of a radiofrequency (RF) source is such that the physical spacing between alternate finger pairs of the IDT corresponds to the wavelength of the SAW (i.e., at the synchronous frequency). In certain embodiments, a RF signal is applied to each IDT of a module, which then generates a SAW that propagates toward the channel. The microfluidic device may further include electronic circuitry for driving the IDTs, receiving and analyzing sensor signals.

The term "acoustic waves" and grammatical equivalents thereof as used herein refer generally to traveling or standing surface acoustic waves and bulk acoustic waves that are created within the solution medium. A surface acoustic wave (SAW) is an acoustic wave propagating along a substrate surface in a direction. In some instances, the surface acoustic waves are Rayleigh waves. Traveling "surface acoustic waves" (TSAWs) enable coupling of surface acoustic waves in a liquid. In some examples, the coupling may be in the form of penetration or leaking of the energy of surface acoustic waves into the liquid, creating bulk acoustic wave (BAW) propagating within the liquid medium. Propagation of the acoustic waves can be performed by streaming the acoustic waves through a liquid. Propagation of acoustic waves may be in a linear direction. In some examples, acoustic waves may propagate across the longitudinal length of the substrate surface. In other examples, acoustic waves may propagate across the width of the substrate surface. In other examples, propagation of acoustic waves may be in a non-linear direction and motion. Propagation of acoustic waves may be conducted in a variety of different ways and by using different materials, including generating an electrical potential by a transducer, such as a series of electrodes. The interference of two or more SAWs may be used to generate two or more BAWs within a region of the substrate surface. These multiple BAWs may give rise to a standing or quasi-standing BAW. Part of the BAW region of the substrate surface may be in mechanical communication with the fluid sample, e.g., in contact with the fluid sample within the channel. A surface supporting a SAW may provide a bounding surface of the channel. In certain embodiments, a tilted angle standing surface acoustic wave is generated.

The interdigitated electrodes may be patterned onto a planar substrate. In some instances, the planar substrate may be a piezoelectric layer. In some examples, the electrodes may be fabricated onto the piezoelectric layer using standard lithography and lift off/wet etching processes. The structure of the electrodes, spacing between electrodes, the number of electrodes (i.e., resolution) on the substrate may vary. In some examples, IDTs or electrodes are used. In some instances, the sample preparation component may include a liquid. In some examples, there may be multiple layers. The different layers may have different arrangement or configuration of scattering structures for scattering acoustic waves.

Systems

The present disclosure also provides systems which find use, e.g., in practicing the subject methods. Systems of the present disclosure include the microfluidic device having two modules, a first module (a debulking or enrichment module) and a second module (a capture or isolation module) and optionally a computer-implemented control system used to activate the IDTs as needed to produce the desired SAW. In some instances, the SAW generated in the subject devices are constant and do not change in amplitude or direction during the implementation of the subject methods. The SAW used in the subject methods, devices, and systems do not substantially perturb laminar flow of sample and other liquids through the microfluidic channels.

The first module may be configured to remove particles smaller than the particles of interest form the sample or to remove particles bigger than the particles of interest form the sample. In the first module, the system may use acoustophoresis to separate particles in a fluid sample by size, as described herein. In certain embodiments, the system includes a first module configured to remove red blood cells and platelets from blood via acoustophoresis. The first module may include a first microfluidic channel having a proximal and distal end and IDTs configured to generate a standing bulk acoustic wave within the first microfluidic channel.

The second module may use a vertical acoustic force to drive particles to a capture surface where the particles of interest in the sample are bound. The second module may include a second microfluidic channel having a proximal and distal end, a capture agent immobilized on a capture surface of the second microfluidic channel, and IDTs configured to generate standing surface acoustic waves through the second microfluidic channel, where the surface acoustic wave generates a vertical acoustic force, where the vertical acoustic force drives the particles of interest towards the capture surface. The second may be used for enrichment of particles of interest by immuno-affinity depletion of non-target particles (negative depletion).

According to the subject embodiments, various types of instrumentation can be used for applying voltage, controlling fluid transport, flow rate and direction within the device. Detection instrumentation may also be applied for detecting or sensing the particle of interest, such instrumentation may include processors, e.g., computers for instructing the controlling instrumentation, receiving data from the detectors, analyzing, storing and interpreting the data, and/or providing the data and interpretations in a readily accessible reporting format, such as on a display.

In some instances, the system may control the input flow rate of the device. The input flow rate refers to the overall flow rate within the microfluidic channel of the microfluidic device. The flow rate will depend upon throughput goals as well as the total area of the channels and the resistance of the channels within the device. In certain embodiments, the subject methods are performed with a sample flow rate of between about 1 μL/min and 100 μL/min, such as 10 μL/min to 40 μL/min. In certain embodiments, the fluid velocity in the sorting region is between about 0.1 mm/s and 4 mm/s, typically in the range of about 2 mm/s.

In some instances, the system may control the input voltage of the device. The IDTs of the device may be coupled to a voltage source. The voltage source may be a direct current source. In some instances, an alternating current voltage source may also be used. In some instances, the subject methods are performed with an input voltage between about 0.04V and 50 V, such as 0.1 V and 1 V. In some instances, the device includes a controller used to control the operation of the microfluidic device by controlling the application of voltage to the IDTs.

Utility

The methods, substrates, systems and kits of the present disclosure find use in a variety of different applications, including applications where it is desirable to isolate, detect, or analyze particles of interest in a liquid sample. Applications of interest include, but are not limited to, cell separation, cell sorting, protein separation and purification, immunoassays, nucleic acid isolation, clinical diagnostics, microfluidics, cell biology research, and the like. The subject methods and devices of the present disclosure allow for introducing a sample into a microfluidic device, separating particles in the sample based on size, and binding particles of interest within the microfluidic channel. The subject method and device also find use in applications where detection of rare cells, e.g., CTCs, stem cells, dendritic cell, endothelial progenitor cells, fibrocytes, T cells, fetal cells is desired.

The following examples are offered by way of illustration and not by way of limitation.

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, dimensions, etc.) but some experimental errors and deviations should be accounted for.

Example 1: Enrichment Module—Lateral Acoustic Force Field

A first module configured to remove red blood cells and platelets from whole blood through acoustophoresis is disclosed. The first module includes at least one microfluidic channel configured to allow fluid flow. The channel has a proximal end and a distal end where fluid flows into the proximal end and out of the distal end. In some examples, the first module includes two or more channels in parallel. In examples, 3, 4, 5, 6, 7, 8, 9, or 10 or more channels can be used in parallel, particularly if the channels are within 7 mm of the acoustic field.

Figure 2A:
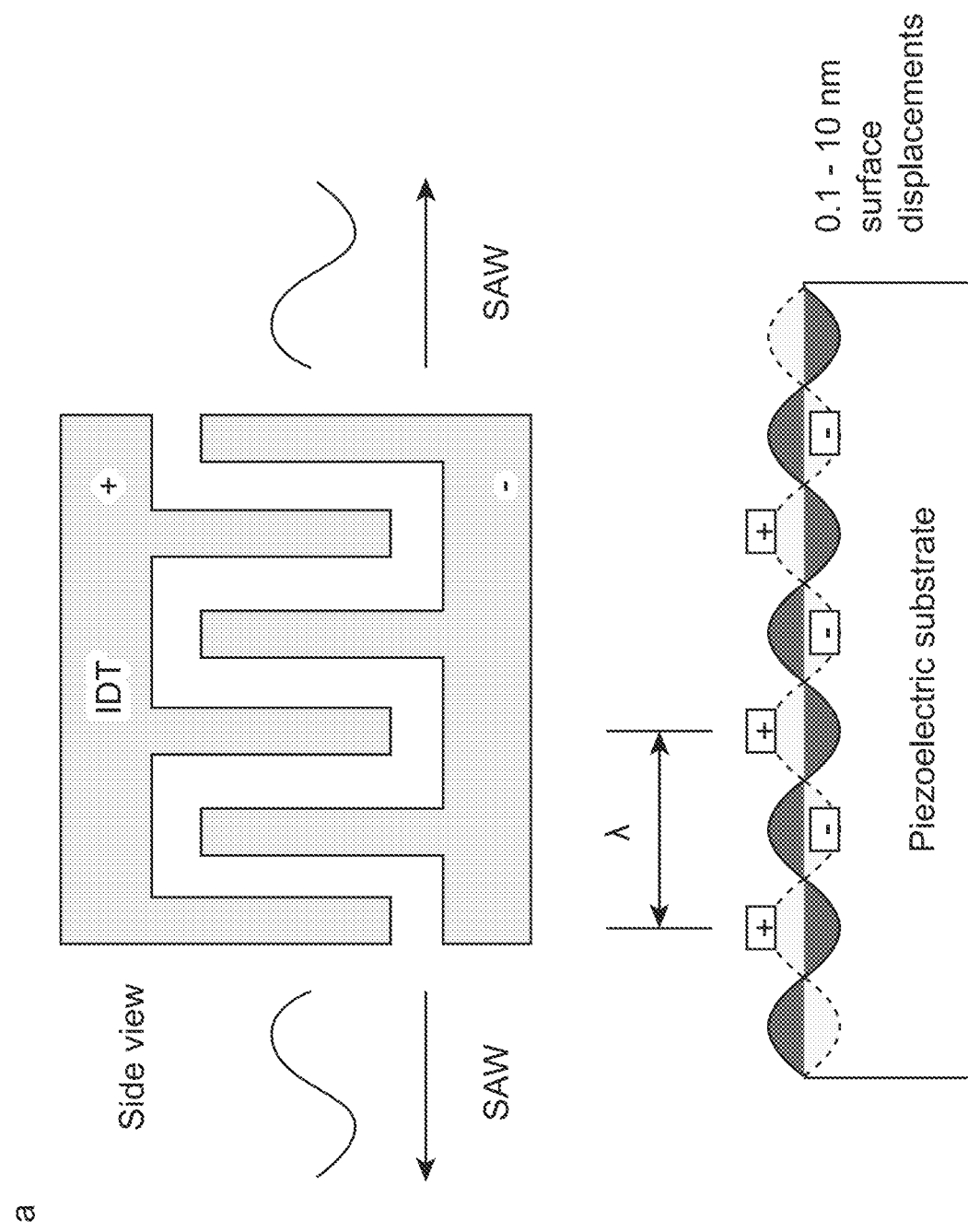
FIG. 2A shows a schematic of surface acoustic wave (SAW) generation from an interdigitated transducer (IDT) fabricated on a piezoelectric substrate.
Figure 2B:
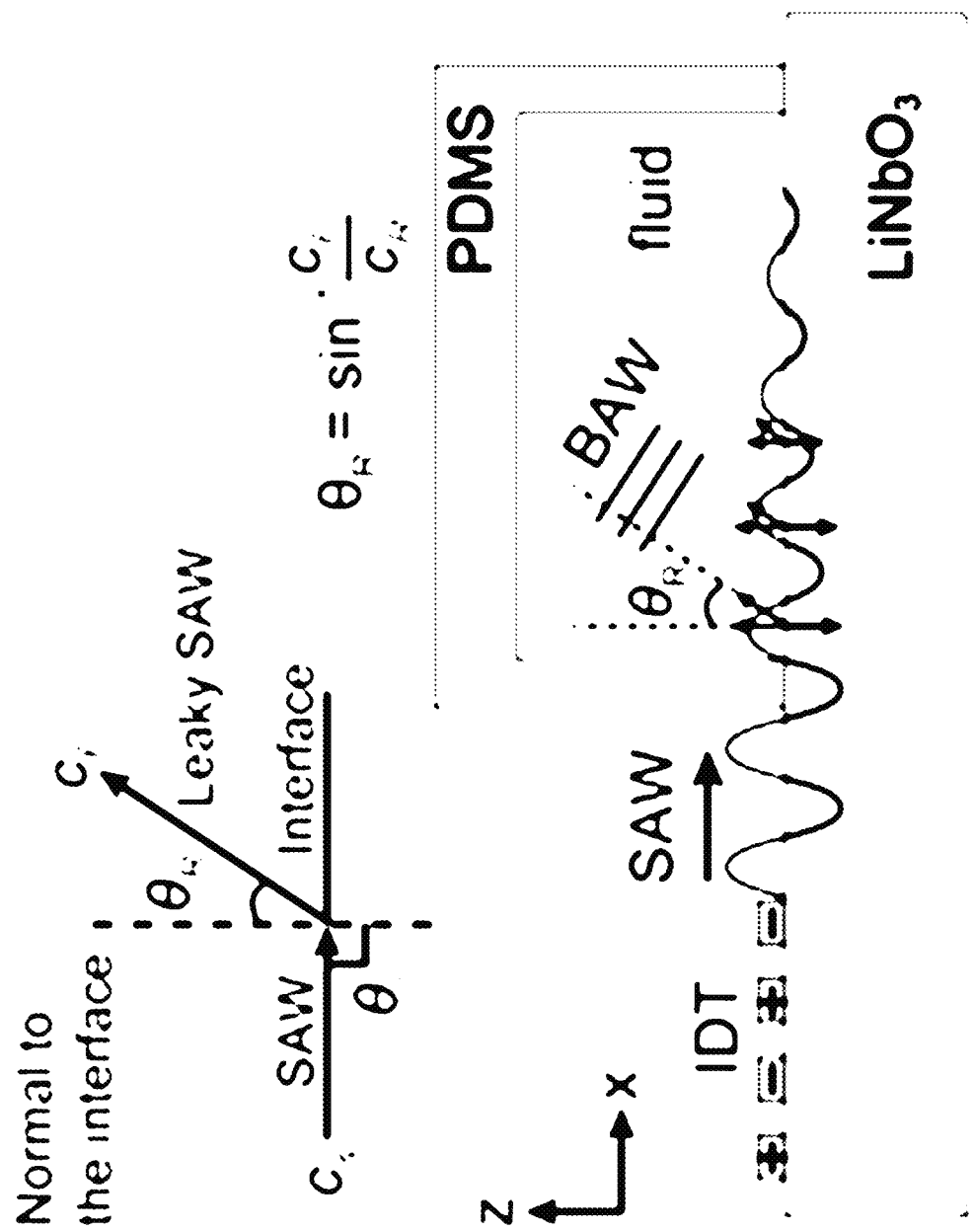
FIG. 2B illustrates the cross-section view of a device comprising of an IDT fabricated on a piezoelectric substrate. A channel defined in a polydimethylsiloxane (PDMS) material is attached to the piezoelectric substrate to create a microfluidic channel. Piezoelectric substrate functions as the bottom channel wall. SAW created by the IDT leaks into the solution environment as it propagates within the microfluidic channel region and induce a compressional acoustic bulk wave (BAW) inside the solution environment.

SAWs in modern lab-on-chip devices are Rayleigh waves composed of elliptical displacement of atoms, bound to the interface between a semi-infinite solid substrate and the surrounding medium. SAWs can be generated on piezoelectric substrates by applying a spatially modulated radio frequency (RF) electric potential using an IDT. Piezoelectric substrate, in turn, generates propagating mechanical stress. Substrates with high electromechanical coupling coefficient (such as lithium niobate—$LiNbO_3$) are preferred to achieve high power conversion efficiencies from RF electrical input to propagating SAWs (Ding, X., et al., Lab on a Chip, 2013. 13(18): p. 3626-3649., Yeo, L. Y. and J. R. Friend, Annual Review of Fluid Mechanics, 2014. 46: p. 379-406.). When IDT finger width and spacing are both $\lambda/4$, $\lambda$ being wavelength, an applied RF signal excites a SAW with $\lambda$, as shown in FIG. 2A. A common implementation of SAW acoustofluidics requires creation of standing bulk acoustic waves in solution environment (Shi, J., et al., Lab on a Chip, 2008. 8(2): p. 221-223; Wood, C., et al., Applied Physics Letters, 2008. 92(4): p. 044104; Shi, J., et al., Lab on a Chip, 2011. 11(14): p. 2319-2324.). As shown in FIG. 2B, propagating SAW refracts into liquid and actuate compressional bulk acoustic wave in fluid once it encounters liquid medium with higher viscosity. The difference between the sound velocity in the liquid and piezoelectric substrate leads to refraction of the SAW into the liquid medium at an angle $\theta$, known as the Rayleigh angle. This refraction behavior could be formulated using Snell's law; $\sin(\theta) = c_f/c_s$, where $c_f$ and $v_s$ are compressional bulk acoustic wave and propagating SAW speeds in fluid and on piezoelectric substrate, respectively. $\theta_r$ is calculated as 22° at water-$LiNbO_3$ interface considering $c_{water}=1490$ m/s and $c_{substrate}=3990$ m/s (propagating in x-direction) for 128° Y-cut $LiNbO_3$ substrate.

Interference principles could be exploited to create standing bulk acoustic wave within the microfluidic channels. Microfluidic technologies based on standing acoustic waves are a technique for noninvasive manipulation and size based sorting of particles, such as cells. In microfluidic devices using SAWs to create BAWs in solution, two identical IDTs located on opposite sides of the microchannel are used. Two counter-propagating SAWs induce a standing BAW pattern in the microchannel region and associated acoustic radiation forces acting on particles, as depicted in FIG. 3A. Radiative acoustic force can be calculated as (Bruus, H., Lab on a Chip, 2011.11(22): p. 3742-3751):

$$F_{rad} = -\nabla U_{rad} = \frac{4\pi r^3}{3}\left[f_1 \frac{1}{2}K_0\langle p_{in}^2\rangle - f_2 \frac{3}{4}\rho_0\langle v_{in}^2\rangle\right] \qquad \text{Equation 1}$$

where $U_{rad}$ is radiation potential, r is particle radius, < > denotes time average, $p_{in}$ and $v_{in}$ are acoustic pressure and particle displacement in fluid. $f_1$ and $f_2$ functions are defined as:

$$f_1(\tilde{K}) = 1 - \frac{K_p}{K_0}; f_2(\tilde{\rho}) = \frac{2(\tilde{\rho}-1)}{2\tilde{\rho}+1} = \frac{2(\rho_p/\rho_0 - 1)}{2\rho_p/\rho_0 + 1}$$

where $K_p$ ($K_D$) and $r_p$ ($r_0$) are bulk compressibility and material density of bioparticle (fluid), respectively. For standing SAW Eq. (1) becomes:

$$F_{rad} = \frac{2\pi^2 r^3}{\lambda}\Phi(\tilde{K},\tilde{\rho})\frac{p_a^2}{\rho_0 c_0^2}\sin\left(\frac{4\pi}{\lambda}y\right); \qquad \text{Equation 2}$$

$$\Phi(\tilde{K},\tilde{\rho}) = \frac{1}{3}\left[\frac{5\tilde{\rho}-2}{2\tilde{\rho}+1} - \tilde{K}\right]$$

Where $p_a$, $c_0$ and y are acoustic pressure amplitude, speed of sound in fluid and particle position along the transverse direction, respectively, whereas ϕ is the acoustic contrast factor. For most bioparticles (RBCs, WBCs, microvesicles, bacteria, etc.) ϕ is positive, indicating that bioparticles are pushed towards the pressure nodes (see FIGS. 3A and 3B) through the lateral acoustic force. $F_{rad}$ in Eq. (2) scales with $r^3$, while the viscous force is proportional to the radius of the particles ($F_v$=−6πηrv, where η and v are fluidic viscosity and particle velocity, respectively). Hence, larger particles experience much larger net forces and therefore move towards the pressure node faster than the smaller ones, as illustrate in FIG. 3B. Acoustophoresis utilizes this size dependent displacement in response to lateral acoustic force to separate differently sized bioparticles. For example, differently sized particles introduced into the microchannel via laterally placed inlet channels initially flow close to the microchannel sidewall. These particles are repositioned at laterally different locations as they move through the standing bulk acoustic wave region. The largest particles reach the center of the microchannel channel before the exit, while small ones remain along the microchannel sidewalls. By splitting the microfluidic flow at the exit region, one can effectively separate different size bioparticles from each other, as illustrated in FIGS. 3A and 3B.

Acoustophoresis is an active separation method that can differentiate bioparticles based on their size, density, compressibility, or a combination of all of these. However, comprehensive studies have shown that the size differences between CTCs and WBCs are marginal for most of the cancer types. Acoustophoresis may not be suitable for isolation of CTCs from comparable sized WBCs. On the other hand, due to its flexible design, easy miniaturization, and integration into microfluidic devices, it could be one of the most efficient on-chip techniques for high-throughput separation of blood components presenting reasonable size and shape differences. Small size RBCs (6-8 μm diameter and 2-2.5 μm thickness) and platelets (2-3 μm) could be readily separated from relatively larger WBCs and CTCs using acoustophoresis. Considering that there are typically 1-10 CTC among ~$10^6$ leukocytes (WBC), ~$10^8$ platelets and ~$10^9$ erythrocytes (RBCs) per ml of blood, on-chip removal of RBCs and platelets before the affinity-based isolation of CTCs could improve CTC capture yields. Therefore, acoustophoresis utilizing lateral acoustic force field was used to remove high abundance RBCs and platelets and feed the output comprising WBCs and CTCs to the acoustic drifting module, as illustrated in FIG. 1.

Figure 3B:
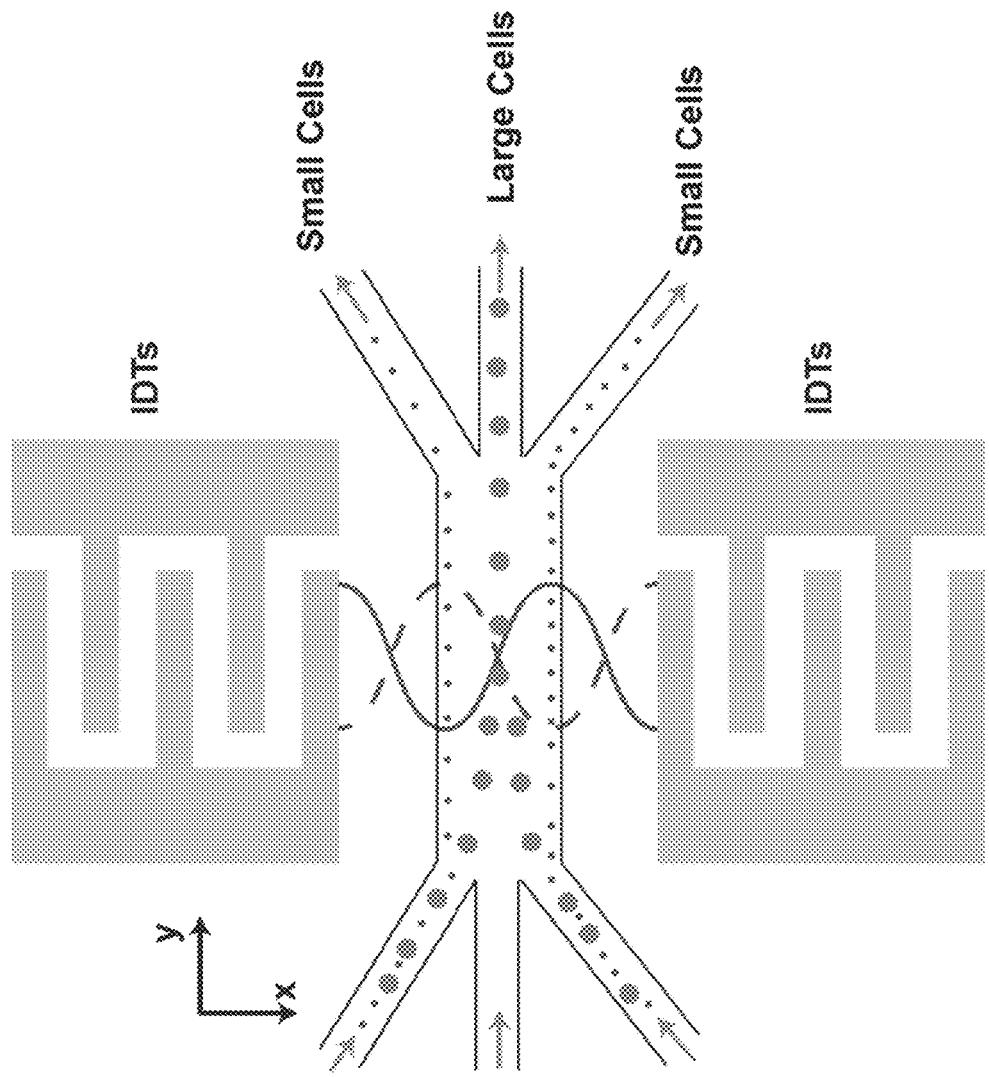
FIG. 3B shows a separation module as known in the art where a lateral standing SAW (along the width of the channel) separates particles based on their size (acoustophoresis). Top view of the acoustophoresis module is shown.

A lab-on-chip debulking (acoustophoresis) module removing the high abundance RBCs and platelets to waste was developed as illustrated in FIG. 3B. The debulking module was designed in a way such that larger cells were kept close to the channel center away from any channel surfaces to minimize surface capturing. This is opposite to the ADE Isolation Module (see Example 2), where the cells were translated towards the capture surfaces using vertical acoustic force field and captured using immobilized agents.

The operating frequency (wavelength λ) of the acoustophoresis device was determined in a way that the dimensions of the target bioparticles must be much smaller than the acoustic wavelength (r/λ<<1). The finger width (w) and pitch (Δ=4λ) of the IDT pairs were determined accordingly. Microfluidic channel dimensions were designed considering the acoustic field node locations and the wavelength of the S SAW. To separate bioparticles that were smaller than 6-8 μm (such as an RBC) from WBCs/CTCs, λ=100 μm to 400 μm wavelength (~13.3 MHz to 530 MHz) acoustic field with a node-to-node distance of λ/2=10 μm to 100 μm was sufficient to satisfy the above criterion for the standing SAW.

The SSAW based platform consists of two parts: a surface acoustic wave chip and a microfluidic channel.

Interdigital transducers were fabricated on 128° YX lithium niobate (LiNbO$_3$) substrate using single step contact photolithography. An S1818 positive resist was used in conjunction with an MF-319 developer to form a sacrificial layer used for electrode patterning. After development, deposition of Ti (5 nm) and Au (120 nm) was performed via electron beam evaporation. To remove the sacrificial layer, the LiNbO$_3$ substrate was sonicated in acetone and rinsed in deionized water to form a pair of IDTs with a period of 300 μm. After fabrication, the LiNbO$_3$ substrate can be diced into individual devices using a diamond scribe.

Figure 6:
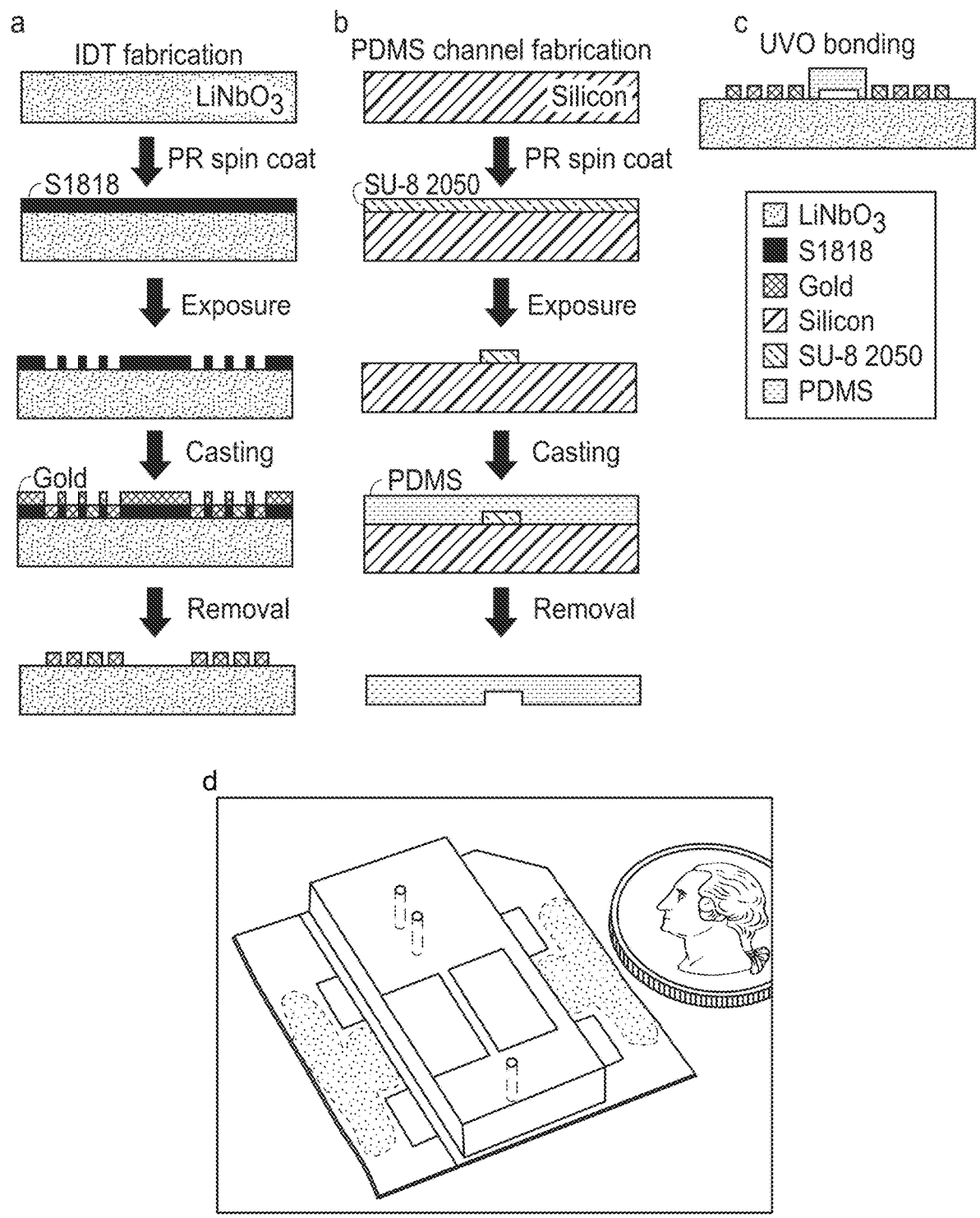
FIG. 6 shows a fabrication scheme for a device consisting of two IDTs and an acoustic cavity formed by attaching a channel formed in a PDMS substrate to the piezoelectric substrate.

The microfluidic channel can be fabricated using standard soft-lithography techniques. An SU-8 2050 photoresist was used to create masters for PDMS casting. Features were developed using an SU-8 developer. A Sylgard 184® silicon elastomer kit was mixed at a 10:1 ratio of elastomer base to curing agent and degassed for 45 minutes prior to casting. After heat curing, the PDMS molds were removed from the silicon master. Individual devices were cut from the casting and their fluid reservoirs were punched into the PDMS molds using a 1.5 mm biopsy punch. Completed devices were cleaned with 2-propanol in an ultrasonic bath for 35 minutes. The microfluidic chip was bonded directly onto LiNbO$_3$ substrate under an upright microscope through matching aligning markers. For sealing purposes, piezoelectric substrate and PDMS layer are clamped through a custom-made acrylic manifold using a Morntec MT-L 1290 CNC laser cutter. A method for forming a microfluidic channel is depicted in FIG. 6.

High Efficiency Conversion of RF Input to Surface Acoustic Waves

The first module included a standing surface acoustic wave chip. The standing surface acoustic wave chip included at least two interdigital transducers. In some examples, the interdigital transducers can be fabricated using photolithography or direct metal deposition using stencils. IDT designs can be optimized using a network analyzer capable of measuring scattering S-parameters. An optimal design must match the IDT resistance (real impedance) to the source resistance. The IDT finger overlap or aperture width (W) is often adjusted so that the IDT design achieves the correct IDT resistance. For acoustophoresis systems where the length requirements for the microfluidic channels and the aperture widths do not match, an L-matching network topology is needed to match the impedances of IDTs to 50Ω. impedance of RF source and coaxial transmission cables (Lee, K., et al., ACS nano, 2015. 9(3): p. 2321-2327).

The surface acoustic wave chip can be used to apply an acoustic force field to the first module such that particles the size of white blood cells (which includes circulating tumor cells) are pushed to an area approximately at the center of the channel while smaller particles (for example, particles the size of red blood cells and platelets), flow through the channel at approximately the sides of the channel. The channel can be branched at the distal end such that the smaller particles flowing at approximately the sides of the channel are directed away from the white blood cell sized particles flowing at approximately the center of the channel. The first module also included interdigitated electrodes that provide sound at an operating frequency.

Figure 7:
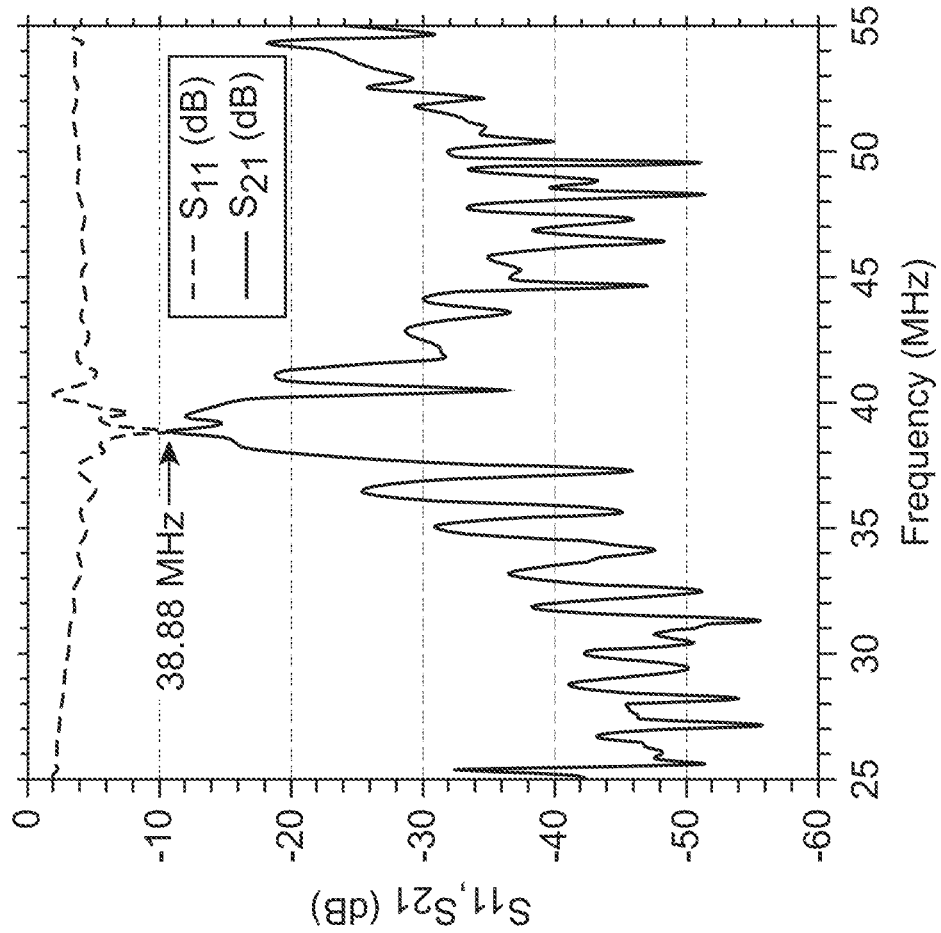
FIG. 7 illustrates an acousto-fluidic chip inside a manifold with S-parameter measurements obtained from the chip.
Figure 7:
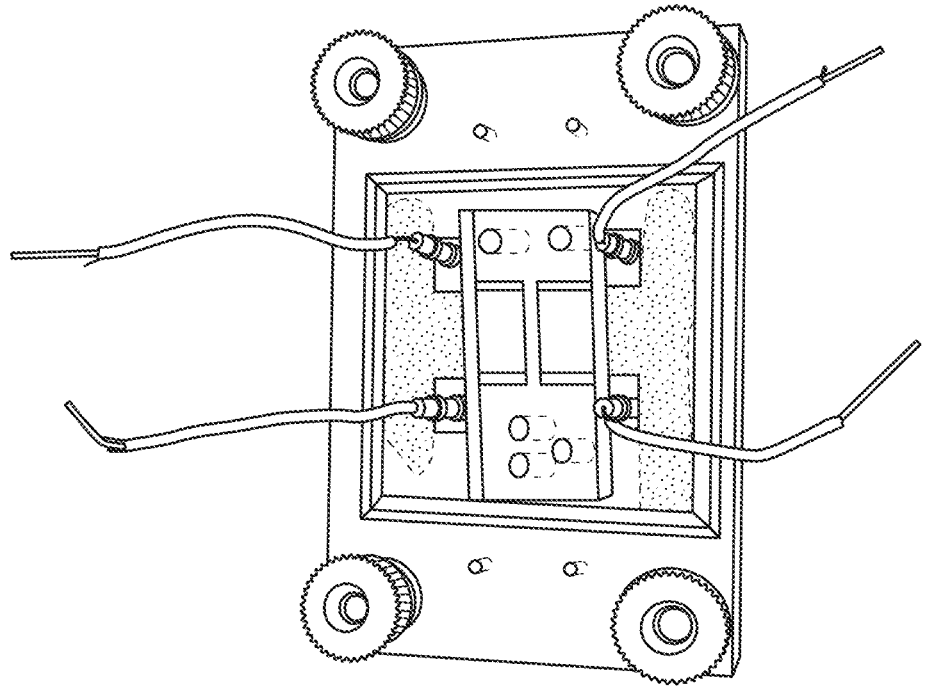

To excite IDTs, a Rigol DG4162 160 MHz digital arbitrary waveform generator with a sampling rate of 500 MHz was employed. IDTs with N=25 pairs, whereas w=D=25 μm were employed. Electrical connections to IDTs were achieved through pogo-type connectors fixed on the top acrylic manifold layer. Printed circuit boards with designed L-matched network components (inductors) and SMA-type plugs could be used. The electrical connections to IDTs and $S_{11}$ and $S_{21}$ parameters are shown in FIG. 7. The experimental data shown in FIG. 7 reveals the quality of the fabricated IDT pairs with a relatively narrow strong resonance peaked at f=38.88 MHz. The resulting SAW speed of 3888 m/s on 128° Y-cut X-propagating LiNbO$_3$ was in very good agreement with the expected value of 3979 m/s. FIG. 7 also shows that insertion loss calculated through 521 was as low as 11 dB. An IDT impedance ($Z_{IDT}$) of about 50+25j Ω (FIG. 7) was obtained. This impedance value is close to the impedances of VNA and coaxial cables (50Ω).

Example 2: Acoustic Drifting Effect (ADE) Module

A second module that captures bioparticles of interest is disclosed. In one particular embodiment, the bioparticles of interest are cells, including circulating tumor cells. The second module includes a microchannel configured to take advantage of the acoustic drifting effect to create a vertical acoustic force field perpendicular to the plane of the capture surface that channels the bioparticles of interest to a capture surface. The capture surface includes capture reagents that specifically bind to markers on the bioparticles of interest. Capture reagents include antibodies such as monoclonal antibodies and/or antibodies specific for markers of circulating tumor cells such as EpCAM. The capture surface can be made of a piezoelectric material.

The second module can also be configured to enrich the target cells with respect to non-target ones by removing the non-target cells using ADE effect and surface capture, a negative depletion approach.

The second module can also be configured to utilize heat for releasing the bioparticles bound to the capture surface. Heat can be provided by acoustic waves. Acoustic waves can be generated through a radiofrequency amplifier or by a Peltier device. The capture surface can also include a protein and/or polymer layer that melts at temperatures between 20° C. and 45° C. in order to facilitate bioparticle release.

The second module can also be configured to utilize acoustic forces to lift the captured cells for downstream analysis.

The second module can also be configured to release bioparticles into an elution solution.

Acoustic Drifting Effect (ADE) enabling rapid advection of bioparticles towards microfluidic channel surfaces is disclosed. ADE, decoupling mass transport from the microfluidic flow, presents a paradigm shift in acousto-microfluidics field by allowing independent control of fluidic shear forces and enhanced mass transport. In preliminary experiments, dramatically enhanced and highly specific target capture on antibody immobilized channel surfaces without disrupting the laminar flow profile is achieved, without creating large shear forces and without using magnetic labels. Bioparticle targets with small diffusion coefficients D=$10^{-8}$ cm/s within 1-2 mm long microfluidic channels in microfluidic flow conditions corresponding to extremely large Peclet numbers (Pe>$10^6$) were used. These conditions correspond to a challenging microfluidic regime with an order of magnitude shorter mixing distances, an order of magnitude larger Peclet numbers and two orders of magnitude smaller diffusion coefficients with respect to a previous milestone work by Stroock et al (Stroock, A. D., et al., Chaotic Mixer for Microchannels. Science, 2002. 295 (5555): p. 647-651.).

Figure 4B:
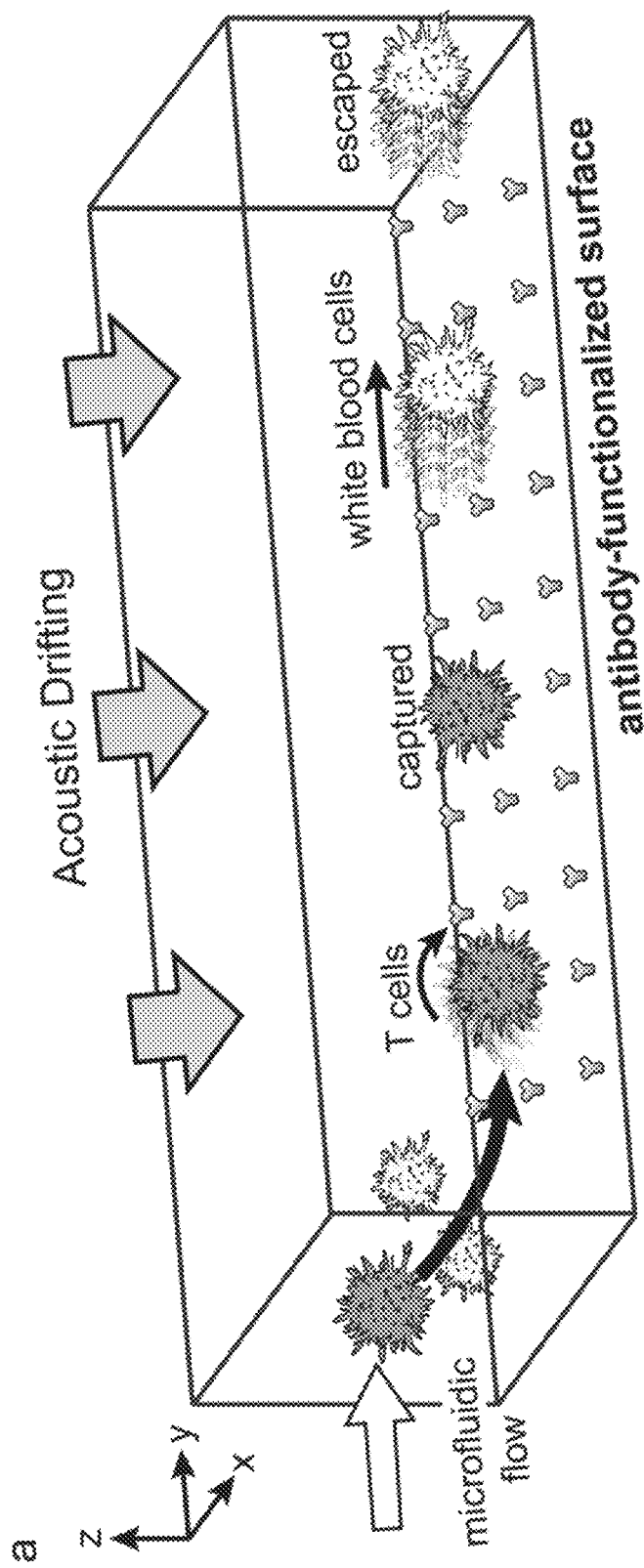
FIG. 4B depicts a three-dimensional view of the immuneaffinity based capturing of specific cells on a substrate using vertical ARF and the associated ADE. This affinity-based isolation technique is entirely different from conventional SAW devices where the ARFs are used for size-based relocation of particles along the cross-section of the channel and size-based separation of particles using different outlets at the end of the acoustic field region, as illustrated in FIG. 3B.

FIG. 5A summarizes the Acoustic Drifting Effect. Superposition of two BAWs propagating in opposite directions produces a pure standing BAW in the horizontal direction with a wavelength $\lambda_{BAW, hori}=\lambda_{SAW}$ sin θ/sin θ=$\lambda_{SAW}$ and simultaneously a pure upward propagating traveling BAW in the vertical direction with wavelength $\lambda_{BAW, hori}=\lambda_{SAW}$ tan $\theta_R$. This traveling BAW interferes with its partially reflection from the roof of PDMS channel and generate a quasi-standing acoustic field in height direction. As illustrated in FIG. 5B, suspended particles which are solely subject to gradient force will be pushed to the pressure node or antinode of standing wave. However, in carefully designed structures that utilizes the vertical BAWs scattered from different interfaces, one can create a vertical quasi-standing acoustic force field. As illustrated in FIG. 5C, Particles in this quasi-standing wave field are subject to two different types of acoustic radiation forces (ARFs): scattering ARF resulted from the non-reflected vertical traveling BAW component, gradient ARF imposed by the vertical standing BAW component. The movement of particles is the result of the competition between scattering ARF and gradient ARF. By carefully choosing the reflection coefficients based on the selections of the materials for the solution and channel materials (i.e. PDMS), the dominating force can be tuned from the scattering ARF to the gradient ARF, or vice versa. By engineering the height of the acoustic cavity, the net force applied on particles which are in the vicinity of the substrate can point downwards to give rise to ADE effect as illustrated in FIGS. 4A and 4B.

Development of CTC Isolation Module

A high-throughput and high-efficiency (capture-yield) rare cell isolation module based on avidin functionalized surfaces will be developed. For device development purposes, cell like bioparticles (fluorescent 5-20 μm diameter dielectric beads coated with biotin) are initially used. Once high-efficiency and high-throughput operation conditions and designs are shown, the device can use serum samples spiked with controlled concentrations of WBCs and rare cells, a representative sample of post-processed whole blood after going through the debulking module as illustrated in FIG. 1. Both high-expression (such as PC3 with 50,000 antigens per cell) and low-expression (such as PC3-9 with 3,000-5,000 antigens per cell) cell lines will be used in these experiments.

Design of Acoustic Drifting Effect Microfluidics to Overcome Mass Transport Limitations Acoustic Drifting Effect is shown to overcome mass transport limitations in microchannels corresponding to fluidic flow conditions with high Peclet number (high convective flow and low diffusion coefficients). ADE is observed in shallow microfluidic channels and associated with the creation of a vertical acoustic force field as a result of acoustic impedance differences in different material interfaces (i.e., water vs PDMS channels). In finite-element (FE) method-based simulations, vertical acoustic field (acoustic pressure gradient) is shown to emerge from the interference of BAWs generated by leaky SAWs radiating into the solution environment and the BAWs reflected from the materials boundaries in the vertical direction, as shown in FIG. 5A. To investigate how this ADE influences the trajectories of particles flowing axially along the y direction, numerical simulations tracing the real-time locations of the particles are performed along the channel in the xz plane (FIG. 5D). For simulations, the particle diameter, channel height and width are chosen to be 7 μm, 80 μm and 1200 μm, respectively. 4 V is applied to a pair of IDTs with 25 numbers of fingers and 150 μm finger spacing. The flow velocity is set to be 1 mm/s. For the convenience of observation and analysis, only the middle region of the channel is examined. For particles entering at random locations along the microfluidic cross-sectional plane, enhanced mass transport of cell size particles to the piezoelectric substrate is shown (FIG. 5D).

Affinity Based Isolation of Bioparticles

Figure 9:
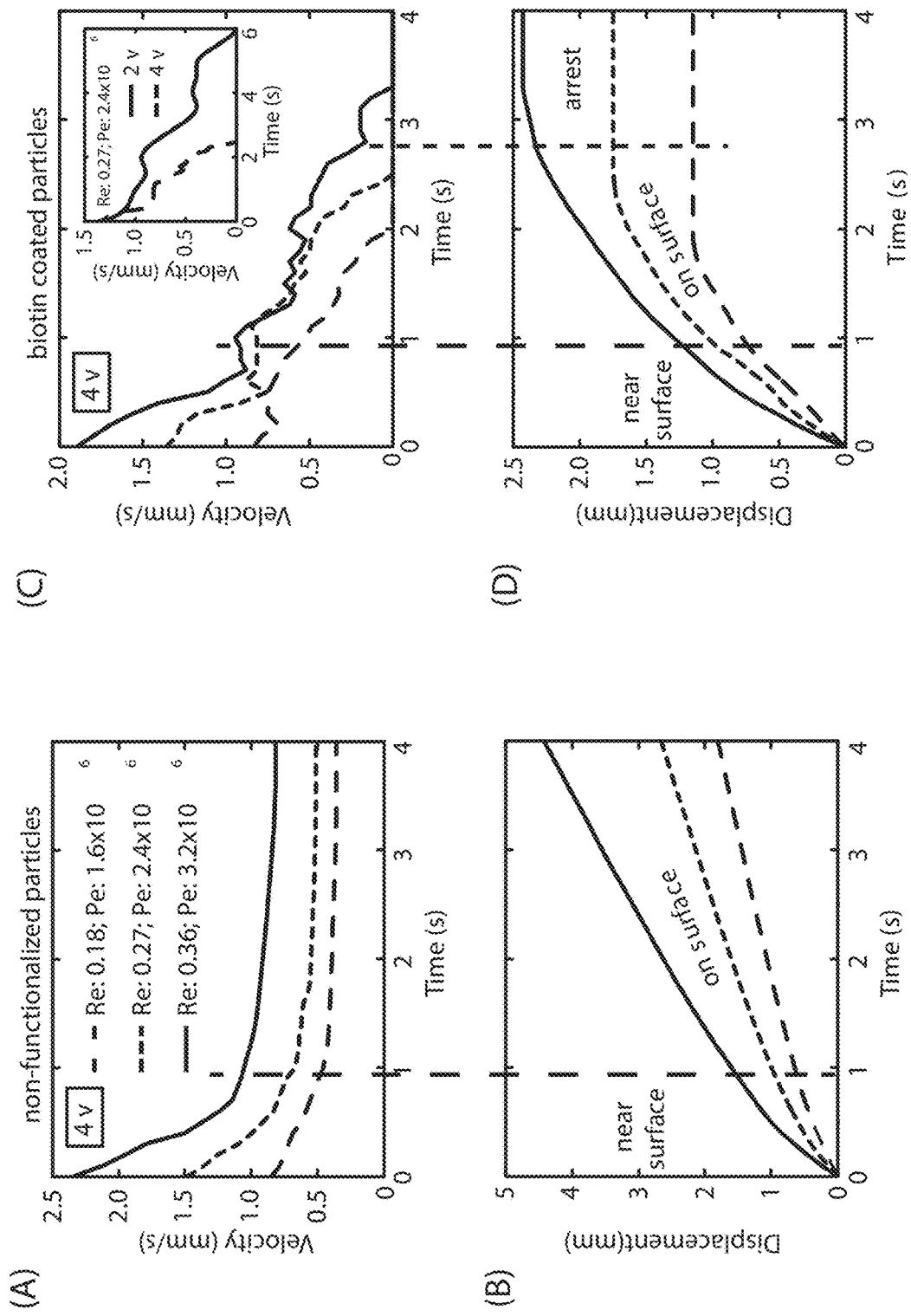
FIG. 9, panels A-D, shows instantaneous velocity and displacement trajectories for (A-B) non-functionalized and (C-D) biotin coated particles that are acoustically drifted to the piezoelectric substrate surface, which is functionalized with avidin proteins. (A) Non-functionalized particles traveling along the channel slow down as they drift towards the piezoelectric substrate where the fluidic flow is slower. Once particles reach the piezoelectric substrate their velocities drop to a constant value. (B) non-functionalized particle displacement becomes a linear function of time as these particles travel at a constant speed on the piezoelectric surface but they cannot be captured on the surface due to fluidic shear forces. (C) Similarly, biotin coated particles slow down as they drift towards the piezoelectric substrate where the fluidic flow is slower. However, biotin coated particles eventually arrest as shown in velocity vs time curve due to specific capturing by the avidin proteins on the piezoelectric surface. (D) Biotin coated particles get arrested at different locations along the channel depending on the flow rates of the fluid indicated by Reynolds (Re) and Peclet (Pe) numbers.

ADE is also experimentally observed in a reliable manner using the device parameters obtained from numerical simulations. In controlled experiments, cell-like particles are used, and Acoustic Drifting Effect is studied in shallow microfluidic channels in the presence of standing and quasi-standing BAWs in the lateral and vertical directions, respectively. To demonstrate that cells can be captured on the ligand coated substrate with high specificity and yield using ADE, biotinylated particles loaded with dye molecules are injected into the fluidic channel, which is bonded on an avidin coated lithium niobate ($LiNbO_3$) substrate. The particle motion and competition between receptor-ligand adhesive bond and surface shear stress were the important factors that determined the capturing efficiency. As shown in FIG. 9A, at 4 V, the non-functionalized (non-specific) particles were rapidly transported towards the surface within 1 seconds and continued to flow at a stable velocity. Because of the lack of the receptor labels, they experienced negligible biomolecular formation force, which was not strong enough compared to the local shear stress. As a result, they continued to move stably on the surface in the channel at a velocity controlled by the laminar flow profile (FIG. 9B). When biotin functionalized particles are targeted, after t=0.5 sec the functionalized particles arrived at the capture surface, continued to decelerate, and then came to a complete rest at t=2-3 sec, as shown in FIG. 9C. The functionalized particles injected at a higher input flow rate (Pe=$3.2\times10^6$) experienced stronger shear stress and translated across a greater distance (2.5 mm at Pe=$3.2\times10^6$ comparing to 1 mm at Pe=$1.6\times10^6$), as predicted.

Figure 10:
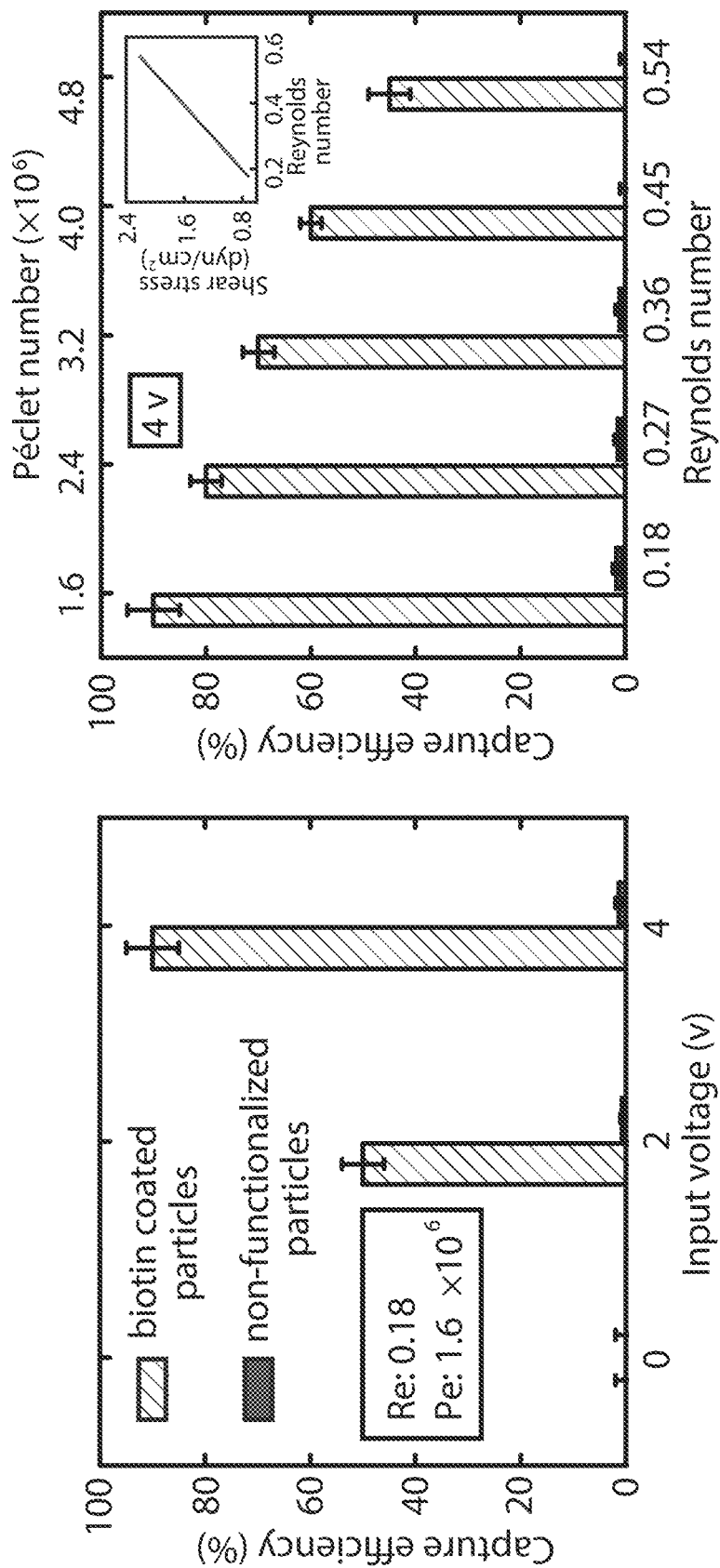
FIG. 10 shows selective capturing of biotin functionalized particles with respect to non-functionalized particles for varying RF power and Peclet numbers.

As shown in FIG. 10, close to ~90% specific capturing of the biotinylated particles with near 100% specificity to the capture agent-avidin is demonstrated. This is remarkable observation given that the microfluidic flow conditions is a regime where Pe>$10^6$.

Development of High-Throughput Isolation Module

Figure 11:
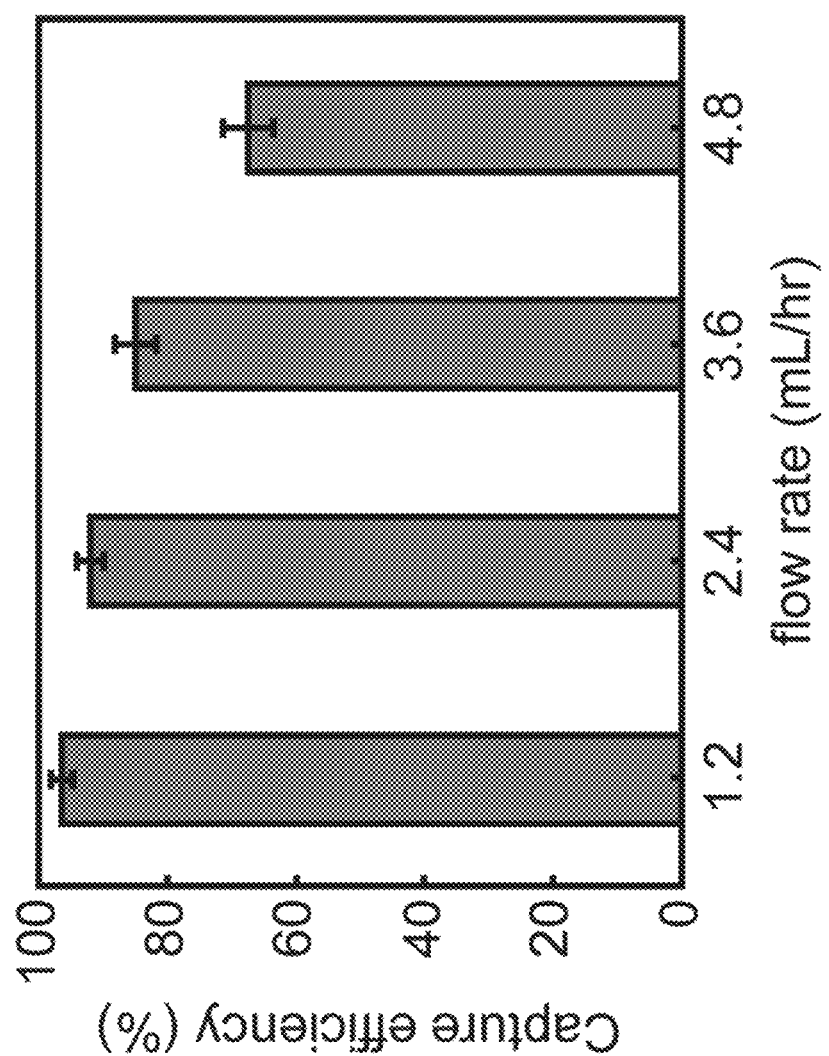
FIG. 11 shows selective capturing of biotin functionalized particles at high fluidic flow rates (1.2 ml/hr-4.8 ml/hr) using two parallel channels functionalized with avidin proteins.
Figure 12:
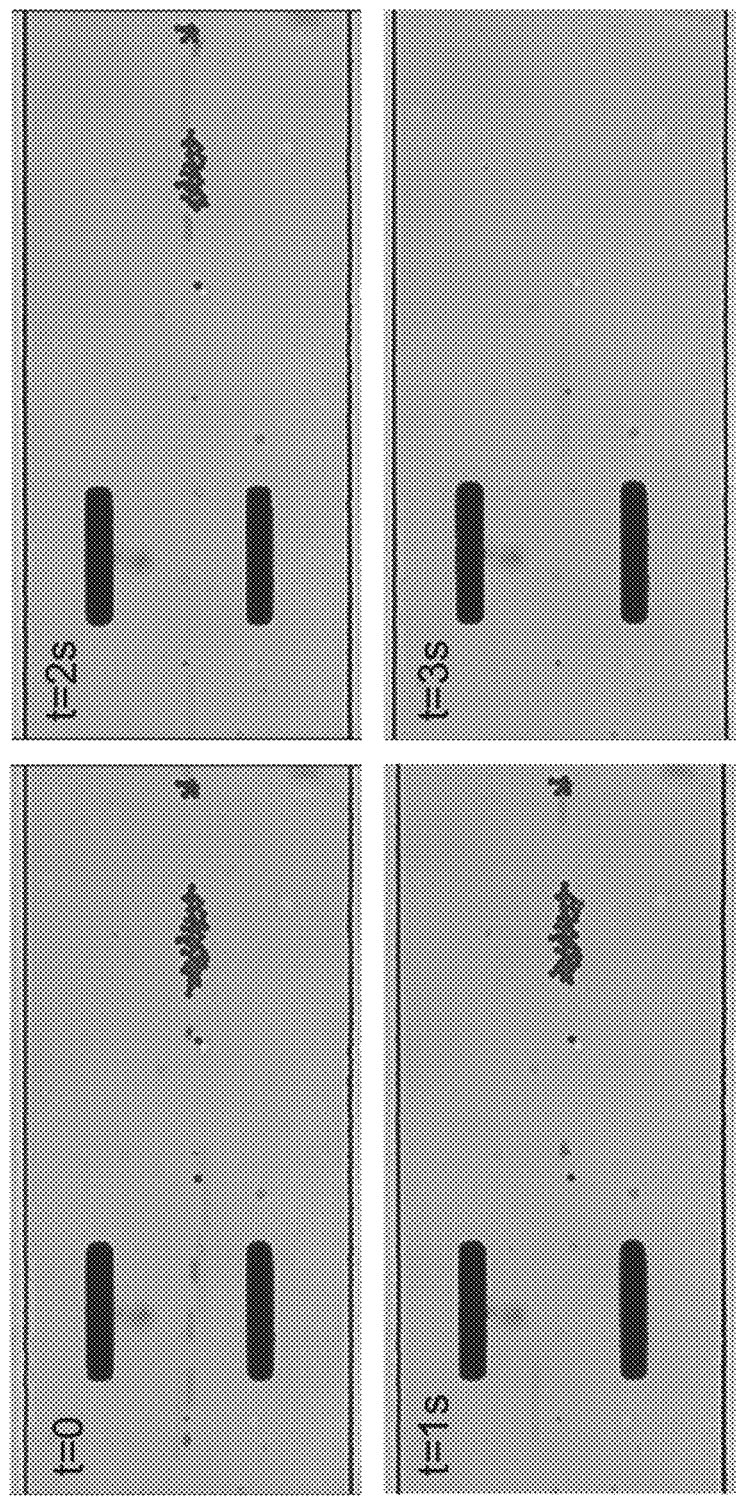
FIG. 12 shows the effective release of captured particles using vertical ARF.

Device parameters for ADE microfluidics were optimized, parallel channels were incorporated to improve the volume throughput, and high efficiency capture of cell like target bioparticles spiked in serum solutions using affinity-based interactions is demonstrated, as shown in FIG. 11 for flow volumes as high as 4.8 ml/hr with capture efficiencies as high as %70. Further, efficiency improvements is possible using longer channel devices.

FIG. 1 provides a schematic of a system that includes a acoustophoresis-based debulking module and an acoustic drifting effect based rare cell (ADE) isolation module. SAWs generated through the IDT electrodes on a flat piezoelectric substrate are used for initial enrichment and subsequent isolation of target cells (CTCs). The debulking module separates RBCs and platelets from WBCs and CTCs in a blood sample using acoustophoresis, a sized based separation technique. The WBCs and CTC enriched using the debulking module are introduced into the CTC isolation module. The CTC isolation module includes a microfluidic channel where capture agents that specifically bind to CTCs are immobilized on an inner surface. Acoustic drifting effect is used to drive the CTCs to the inner surface where the capture agents are immobilized for affinity-based separation of CTCs from WBCs in the CTC isolation module. Finally, combined acoustic heating and lifting forces using SAWs is used for acoustic release of captured CTCs and the released CTCs are collected in a fluid flowed through the microchannel and the fluid with the CTCs is subjected to downstream analysis.

FIG. 2A illustrates a metallic IDT deposited on the piezoelectric substrate that generates SAWs that propagate along the piezoelectric substrate surface in both directions.

FIG. 2B shows a side view of the device. The SAWs (Rayleigh waves) are coupled with the fluid to form propagating BAW responsible for radiative acoustic force acting on particles. The BAW propagates in the fluid at the Rayleigh angle (00.

FIG. 3A illustrates a pair of IDTs that are used to create SSAWs within a microfluidic channel region. The SSAWs produce a pressure node in the center of the microchannel. Bioparticles with positive contrast factor are displaced towards the pressure node by the acoustic radiation force. The larger particles experience much larger net forces and therefore move towards the pressure node faster than the smaller ones (bottom illustration). Shi, J., et al., *Continuous particle separation in a microfluidic channel via standing surface acoustic waves* (SSAW). Lab on a Chip, 2009. 9(23): p. 3354-3359.

FIG. 3B provides a schematic of a top view of a lateral acoustic force field generated by two pairs of IDTs located across the microfluidic channel. The SSAWs generated by the laterally placed pairs of IDTs include a pressure node located in the center of the microfluidic channel. The sample is introduced using two inlets connected to the lateral regions of the microchannel and optionally, buffer is introduced through an inlet that directs the buffer towards the central region of the microchannel. The particles present in the sample initially flow close to the microchannel sidewall. As the particles move through IDT regions, larger particles (e.g., WBCs, CTCs, etc.) experience a larger acoustic force and move towards the pressure nodes located in the center of the microchannel. Smaller particles (such as RBCs, platelets) do not experience the acoustic force and remain located towards the sides of the channel Dividing the fluid flow at the exit region such that an outlet(s) is positioned along sides of the microchannel and an outlet is positioned along the center of the microchannel can effectively separate differently sized bioparticles from each other.

FIG. 4A provides a schematic of the affinity-based isolation of cells facilitated by the vertical ARF. Cells are pushed in a perpendicular direction to the laminar fluidic flow line towards the antibody-immobilized surface by application of this vertical acoustic force. The application of vertical acoustic force does not disrupt the laminar flow profile such that while local shear force close to the surface is diminished due to the laminar flow profile, there is enough shear force to remove non-specifically bound cells.

FIG. 4B shows a three-dimensional illustration of the ADE on cell trajectories within a microfluidic channel.

FIG. 5A provides simulations showing the pressure field profile when PDMS is treated as a hyperelastic medium. Here, BAWs are created by the refraction of the counter-propagating SAWs within an acoustic cavity created by the PDMS surface and piezoelectric substrate. BAWs are trapped within the acoustic cavity formed by the multiple impedance-mismatched boundaries, as shown in the figure.

FIG. 5B illustrates the ARF created in the lateral direction as a result of lateral standing BAW.

FIG. 5C illustrates the ARF created in the vertical direction as a result of vertical quasi-standing BAW, which is a superposition of a vertical traveling and vertical standing BAW components. Suspended particles in this quasi-standing wave field are subject to two different types of acoustic radiation forces (ARFs): scattering ARF resulted from the non-reflected vertical traveling BAW component, gradient ARF imposed by the vertical standing BAW component.

FIG. 5D shows FE simulations illustrating the effect of the lateral and vertical ARFs acting on particles traveling along the channel. Particles are focused along the channel at the piezoelectric substrate surface.

FIG. 6 provides a fabrication scheme for a microfluidic device that includes IDTs fabricated in a piezoelectric substrate and a microchannel formed in a PDMS substrate and bonded to the piezoelectric substrate. IDTs are fabricated using photolithography and lift-off processes. Microfluidic channels are fabricated using soft lithographic techniques.

FIG. 7 illustrates an acoustofluidic chip inside a custom-made manifold. S-parameter measurements demonstrate a strong match between the electrical load and the source impedance.

FIG. 8 shows that the laminar profile is not affected by the ADE.

FIG. 9A-9B provides a comparison of the velocity and displacement trajectories between functionalized and non-functionalized particles. FIG. 9A shows that non-functionalized particles initially move near the surface under the effect of ADE, but do not get captured on the avidin-coated substrate due to minimal interaction with the substrate. The velocity for Re=0.18; Pe=$1.6\times10^6$ ranges from 900 to 1000 µm/s. The velocity for Re=0.27; Pe=$2.4\times10^6$ ranges from 1400 to 1500 µm/s. The velocity for Re=0.36; Pe=$3.2\times10^6$ ranges from 2000 to 2200 µm/s.

FIG. 9C-9D shows that the functionalized particles initially decelerate near the surface in the presence of a SSAW field and then continues to decelerate on the surface due to the biomolecular interaction between biotin and avidin until it eventually arrests on the surface. When t=0, the velocity for Re=0.18; Pe=$1.6\times10^6$ is less than −800 µm/s. When t=0, the velocity for Re=0.27; Pe=$2.4\times10^6$ is approximately 1400 µm/s. When t=0, the velocity for Re=0.36; Pe=$3.2\times10^6$ is approximately 1800 µm/s.

FIG. 10 shows that for a fixed input flow rate, a higher voltage leads to a higher capture efficiency for functionalized particles. The capture efficiency for functionalized particles in absence of vertical acoustic force was negligible. At 4 Volts, the vertical acoustic force resulted in capture of the functionalized particles at a capture efficiency of about 90%. This data shows that at the flow rate tested, immuno-affinity capture of the functionalized particles is extremely limited in absence of the vertical acoustic force (ADE). The capture efficiency for non-functionalized particles at 4 V was less than 5%. FIG. 10 also shows that for a fixed input voltage (4 V), capture efficiency decreases with increasing Peclet number. The inset depicts the relationship of shear stress to Reynolds number. Functionalized particles depicted close to 90% capture efficiency at 0.18 Reynold number (about 0.84 dyn/cm$^2$ shear stress) and $1.6\times10^6$ Peclet number. The capture efficiency for the functionalized particles decreased to about 80% at 0.27 Reynold number (about 1.26 dyn/cm$^2$ shear stress) and $2.4\times10^6$ Peclet number and to about 70% at 0.36 Reynold number (about 1.68 dyn/cm$^2$ shear stress) and $3.2\times10^6$ Peclet number. Non-specific capture also decreases at higher Reynolds and Peclet numbers. The capturing process was completed within a channel region that is shorter than 2 mm. The capture efficiency for non-functionalized particles at 4V ranged from less than 10% to 0% depending on the follow conditions.

Example 3: Acoustic Release of Captured Particles

Cells captured by the ADE Isolation module can be acoustically released. Acoustic heating is suitable for neutralizing the molecular bonds anchoring cells to the piezoelectric substrate. ARF can also help lifting up the captured bioparticles. Acoustic release of captured particles is experimentally shown.

It is also possible to make use of protein/polymer layers that are known to be heat sensitive and melt at temperatures higher than room temperature but not high enough to harm cells. FIG. 11 illustrates the effective release of captured bioparticles after 3 seconds of application of acoustic field heating. The effect was a combination of protein neutralization and acoustic pressure created at the capture surface. This process may be studied using infrared-imaging and temperature sensitive polymers.

What is claimed is:

1. A method of isolating target particles from a fluid sample, the method comprising:
    flowing a sample into a microfluidic channel of a microfluidic device, the sample comprising or suspected of comprising target particles and non-target particles, the microfluidic channel comprising a piezoelectric substrate comprising an inner surface on which capture agents that specifically bind to the target particles are immobilized;
    applying a vertical acoustic force generated from standing surface acoustic waves (SSAWs) to the sample, wherein the vertical acoustic force drives the target particles and non-target particles to the inner surface of the piezoelectric substrate thereby promoting binding of the target particle to the capture agents, whereas the non-target particles flow away from the piezoelectric substrate with the flowing sample; and
    eluting the target particles bound to the capture agents.

2. A method of isolating a target particle from a fluid sample, the method comprising:
    flowing the sample in a laminar flow profile into a microfluidic channel of a microfluidic device, the sample comprising or suspected of comprising target particles and non-target particles, the microfluidic channel comprising a piezoelectric substrate comprising an inner surface on which capture agents that specifically bind to the target particles are immobilized;
    applying a vertical acoustic force generated from standing surface acoustic waves (SSAWs) to the sample, wherein the vertical acoustic force drives the target particles and non-target particles to the inner surface of the piezoelectric substrate thereby promoting binding of the target particle to the capture agents, whereas the non-target particles flow away from the piezoelectric substrate with the flowing sample; and
    eluting the target particles bound to the capture agents.

3. A method of isolating a target particle from a fluid sample, the method comprising:
    a) flowing the sample in a laminar flow profile into a microfluidic channel of a microfluidic device,
        the sample comprising or suspected of comprising target particles and non-target particles,
        the microfluidic channel comprising an acoustic cavity comprising at least one surface formed from an elastic material and at least one surface formed from a piezoelectric substrate, capture agents that specifically bind to the target particles immobilized on an inner surface of the piezoelectric substrate, the microfluidic device comprising two interdigitated transducers (IDTs) positioned across the width of the microfluidic channel and configured to generate traveling surface acoustic waves (SAWs) within the microfluidic channel, wherein the SAWs refract upon interaction with a fluid sample present in the microfluidic channel thereby generating incident compressional bulk acoustic waves (BAWs), wherein the BAWs are reflected in the acoustic cavity, wherein the reflected BAWs interfere with the incident BAWs and generate a vertical acoustic force in the microfluidic channel, wherein the vertical acoustic force drives the target particles towards the inner surface of the piezoelectric substrate;

b) activating the IDTs;

c) applying the vertical acoustic force to the sample to drive the target particles towards the inner surface of the piezoelectric substrate thereby promoting binding of the target particle to the capture agents, whereas the non-target particles flow away from the piezoelectric substrate with the flowing sample; and d) eluting the target particles bound to the capture agents.

4. The method of claim 1, wherein the fluid sample is flowing through the microfluidic channel at a velocity ranging from 0.5 mm/s-3 mm/s.

5. The method of claim 1, wherein the fluid sample is a blood, serum, or plasma sample.

6. The method of claim 1, wherein the target particle is 30 nm to 500 μm in diameter and wherein the target particle of interest has a compressibility factor of $2\times10^{-10}$ Pa$^{-1}$-$5\times10^{-10}$ Pa$^{-1}$.

7. The method of claim 1, wherein the target particle is a circulating tumor cell (CTC), endothelial progenitor cell, or bacteria.

8. The method of claim 1, wherein the capture agent comprises an antibody that specifically binds to the target particle.

9. The method of claim 2, wherein the fluid sample is flowing through the microfluidic channel at a velocity ranging from 0.5 mm/s-3 mm/s.

10. The method of claim 2, wherein the fluid sample is a blood, serum, or plasma sample.

11. The method of claim 2, wherein the target particle is 30 nm to 500 μm in diameter and wherein the target particle of interest has a compressibility factor of $2\times10^{-10}$ Pa$^{-1}$-$5\times10^{-10}$ Pa$^{-1}$.

12. The method of claim 2, wherein the sample is an enriched sample from which non-target particles have been removed.

13. The method of claim 2, wherein the target particle is a circulating tumor cell (CTC), endothelial progenitor cell, or bacteria.

14. The method of claim 2, wherein the capture agent comprises an antibody that specifically binds to the target particle.

15. The method of claim 3, wherein the fluid sample is flowing through the microfluidic channel at a velocity ranging from 0.5 mm/s-3 mm/s.

16. The method of claim 3, wherein the fluid sample is a blood, serum, or plasma sample.

17. The method of claim 3, wherein the target particle is 30 nm to 500 μm in diameter and wherein the target particle of interest has a compressibility factor of $2\times10^{-10}$ Pa$^{-1}$-$5\times10^{-10}$ Pa$^{-1}$.

18. The method of claim 3, wherein the sample is an enriched sample from which non-target particles have been removed.

19. The method of claim 3, wherein the target particle is a circulating tumor cell (CTC), endothelial progenitor cell, or bacteria.

20. The method of claim 3, wherein the capture agent comprises an antibody that specifically binds to the target particle.

\* \* \* \* \*